(12) United States Patent
Tanner et al.

(10) Patent No.: US 9,920,358 B2
(45) Date of Patent: Mar. 20, 2018

(54) HELICASE SUPPRESSION OF NON-TEMPLATE AMPLIFICATION

(71) Applicant: New England Biolabs, Inc., Ipswich, MA (US)

(72) Inventors: Nathan Tanner, Peabody, MA (US); Thomas C. Evans, Jr., Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 609 days.

(21) Appl. No.: 14/385,674

(22) PCT Filed: Jun. 27, 2014

(86) PCT No.: PCT/US2014/044492
§ 371 (c)(1),
(2) Date: Sep. 16, 2014

(87) PCT Pub. No.: WO2014/210416
PCT Pub. Date: Dec. 31, 2014

(65) Prior Publication Data
US 2016/0237483 A1  Aug. 18, 2016

Related U.S. Application Data

(60) Provisional application No. 61/840,287, filed on Jun. 27, 2013.

(51) Int. Cl.
*C12P 19/34* (2006.01)
*C12Q 1/68* (2018.01)

(52) U.S. Cl.
CPC ......... *C12Q 1/6853* (2013.01); *C12Q 1/6848* (2013.01)

(58) Field of Classification Search
USPC .............................................. 435/6.12, 91.2
See application file for complete search history.

(56) References Cited

U.S. PATENT DOCUMENTS

| 7,282,328 B2 | 10/2007 | Kong et al. | |
| 2010/0285473 A1* | 11/2010 | Wolff | C12Q 1/6844 435/6.1 |
| 2012/0021460 A1* | 1/2012 | Lowe | C12Q 1/6844 435/91.2 |

OTHER PUBLICATIONS

Schlotterer, et al., Nucleic Acids Research, 20(2): 211-215 (1992).
Ogata, et al., Nucleic Acids Research, 26(20): 4657-4661 (1998).
Brukner, et al., Analytical Biochemistry, 339:345-347 (2005).
Chakrabarti, et al., Nucleic Acids Research, 29:2377-2381 (2001).
Perales, et al., Nucleic Acids Research, 31(22):6473-6480 (2003).
Fukui, et al., International Journal of Molecular Science, 14:6436-6453 (2013).
Tanner, et al., Biotechniques, 53:81-89 (2012).
An, et al., J. Biol Chem, 208 (32):28952-28958 (2005).
Nagamine, et al., Molecular and Cellular Probes, 16:223-229 (2002).
Notomi, et al., Nucleic Acids Research, 28:e63 (2000).

* cited by examiner

*Primary Examiner* — Kenneth R Horlick
(74) *Attorney, Agent, or Firm* — New England Biolabs, Inc.; Harriet M. Strimpel

(57) ABSTRACT

Provided herein is a method for reducing amplification of non-template molecules in a nucleic acid sample. In certain embodiments, the method involves adding a helicase to a reaction mixture for non-helicase-dependent amplification of target nucleic acid.

20 Claims, 8 Drawing Sheets

HELICASE SUPPRESSION OF NON-TEMPLATE AMPLIFICATION

CROSS REFERENCE

This application is a § 371 application of international application number PCT/US2014/044492 filed on Jun. 27, 2014, which claims priority from U.S. provisional application No. 61/840,287, filed on Jun. 27, 2013, herein incorporated by reference.

BACKGROUND

DNA amplification is frequently used in DNA diagnostic tests and sequencing protocols. Both require a low background of non-specific amplification. Unfortunately, amplification methods that utilize primers appear to give rise to false positive signals of non-template DNA that affect the quality of the results (Schlötterer and Tautz, *Nucleic Acids Research*, 20 (2):211-215 (1992); Ogata and Miura, *Nucleic Acids Research*, 26(20):4657-4661 (1998); Brukner, et al., *Analytical Biochemistry*, 339:345-347 (2005)). These false positive signals can be detected in control samples with non-template DNA or no DNA. Without wishing to be limited by theory, it is believed that false positives predominantly result from transient primer secondary structure formation and primer dimers.

Improvements in amplification signal and amplification specificity have not removed the adverse effects of background signal for isothermal amplification reactions. Chakrabati, et al., *Nucleic Acids Research*, 29:2377-2381 (2001), described enhancement of polymerase chain reaction (PCR) amplification using single low molecular weight amide additives. However, use of organic compounds is not compatible with all platforms.

Proteins and enzymes have been added in addition to the DNA polymerase for amplification reactions. These include single-stranded DNA binding proteins, clamps, and recombination proteins (Perales, et al, *Nucleic Acids Research*, 31(22):6473-6480 (2003); Fukui et al, *Int J Mol Sci*, 14:6436-6453 (2013)). Similarly, "hot start" approaches inhibit DNA polymerases in a temperature-dependent manner (U.S. Pat. No. 5,338,671). These methods may improve reaction performance but cannot eliminate non-template amplification at reaction temperatures.

SUMMARY

In general a reaction mixture is provided that includes: a nucleic acid sample comprising a template; nucleotides; four or more primers; a polymerase; and a helicase; wherein the reaction mixture does not contain a single-stranded DNA binding protein (SSBP) and wherein the reaction mixture is capable of amplifying the template when placed under isothermal or polymerase chain reaction conditions.

In one aspect, the helicase is a thermostable helicase. In another aspect, the helicase is a PcrA/UvrD/Rep helicase. In another aspect, the helicase is *Thermoanaerobacter tengcongensis* (Tte) helicase (SEQ ID NO:19), *Thermus thermophilus* (Tth) helicase (SEQ ID NO:20) or *Aquifex aeolicus* (Aq793) helicase (SEQ ID NO:21).

In one aspect, the template is DNA or RNA or both and the polymerase is a strand-displacing polymerase such as a Bst polymerase, a polD polymerase, a 9° N polymerase or phi29 polymerase. In another aspect, the polymerase is a thermostable polymerase. In another aspect, the template is RNA and the polymerase is a reverse transcriptase. In another aspect, the template is genomic DNA.

In general, a method is provided for reducing amplification of non-template molecules from a nucleic acid sample, that includes: incubating a reaction mixture that contains a nucleic acid sample comprising a template, nucleotides, at least four primers, a polymerase, and a helicase under amplification conditions, and amplifying the template; wherein the amplification reaction is not helicase dependent but wherein the helicase reduces amplification of non-template molecules.

In one aspect, the amplification conditions are isothermal amplification conditions. In another aspect, amplifying the template results in whole genome amplification or one or more target fragments of a genome or cDNA or amplifying cDNA after reverse transcription of the RNA. In one aspect, the amplification conditions include thermocycling. In one aspect, the method further includes quantifying the amount of amplified template. In one aspect, the helicase is a PcrA/UvrD/Rep helicase such as for example, a *Thermoanaerobacter tengcongensis* (Tte) helicase, *Thermus thermophilus* (Tth) helicase or *Aquifex aeolicus* (Aq793) helicase. In one aspect, the polymerase a Bst polymerase, a polD polymerase, 9° N polymerase or phi29 polymerase.

In general, a method is provided for inhibiting non-helicase-dependent amplification of non-target nucleic acids, comprising: adding a helicase to a reaction mixture for non-helicase-dependent amplification of target DNA; and inhibiting false positive signal from non-helicase-dependent amplification of non-target nucleic acids.

Reactions with template (lambda) DNA are represented by solid lines and reactions without template by dashed lines. In the absence of helicase, both positive and negative reactions produce amplification threshold times. With the addition of sufficient amount of helicase (in a 25 µl reaction mixture containing >7 ng Tte, >10 ng Tth, or >0.02 µL Aq793 lysate with a Bst polymerase, the negative reaction is completely inhibited while a rapid threshold of the positive reaction is maintained. The absence of an amplification signal is plotted as the maximum reaction time (83.3 minutes, "No Signal" dashed line) for comparison.

Figure 4:
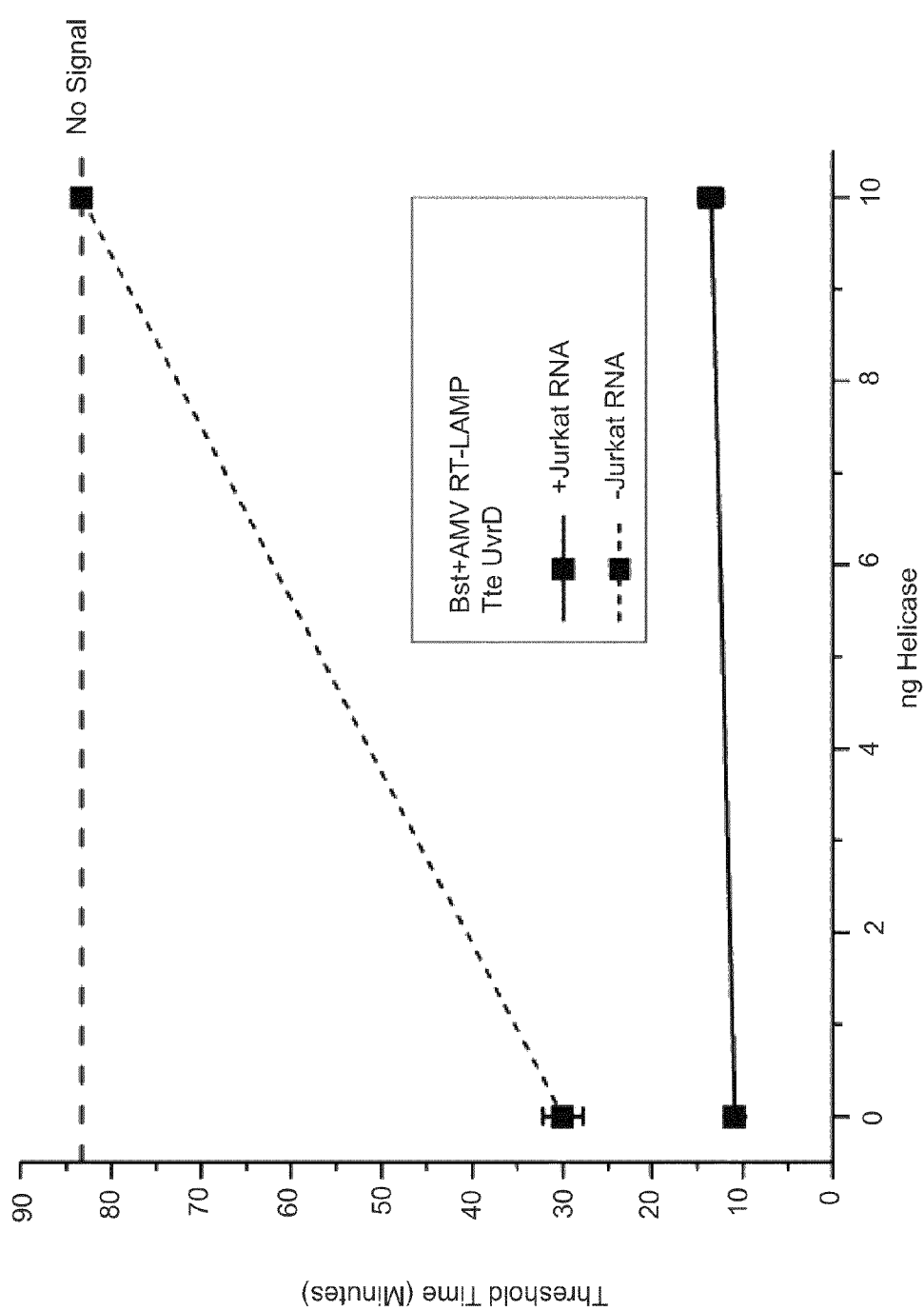

FIG. 4 shows the effect of a helicase on non-template amplification in reverse transcription LAMP (RT-LAMP). Reactions were performed using RNA template (Jurkat total RNA) or avian myeloblastosis virus (AMV) reverse transcriptase in addition to LAMP buffer, primers, and Bst DNA polymerase. Threshold time in minutes is plotted on the y-axis against nanograms of Tte helicase on the x-axis. Reactions with template RNA are represented by solid line and reactions without template RNA dashed line. Without addition of helicase, positive reactions resulted in a threshold of approximately 10 minutes while negative reaction gave a threshold of approximately 30 minutes. With the addition of 8 ng Tte helicase, the positive reaction maintained a threshold of 10 minutes while the negative reaction was completely inhibited (plotted as maximum reaction time, 83.3 minutes, for comparison).

Figure 5:
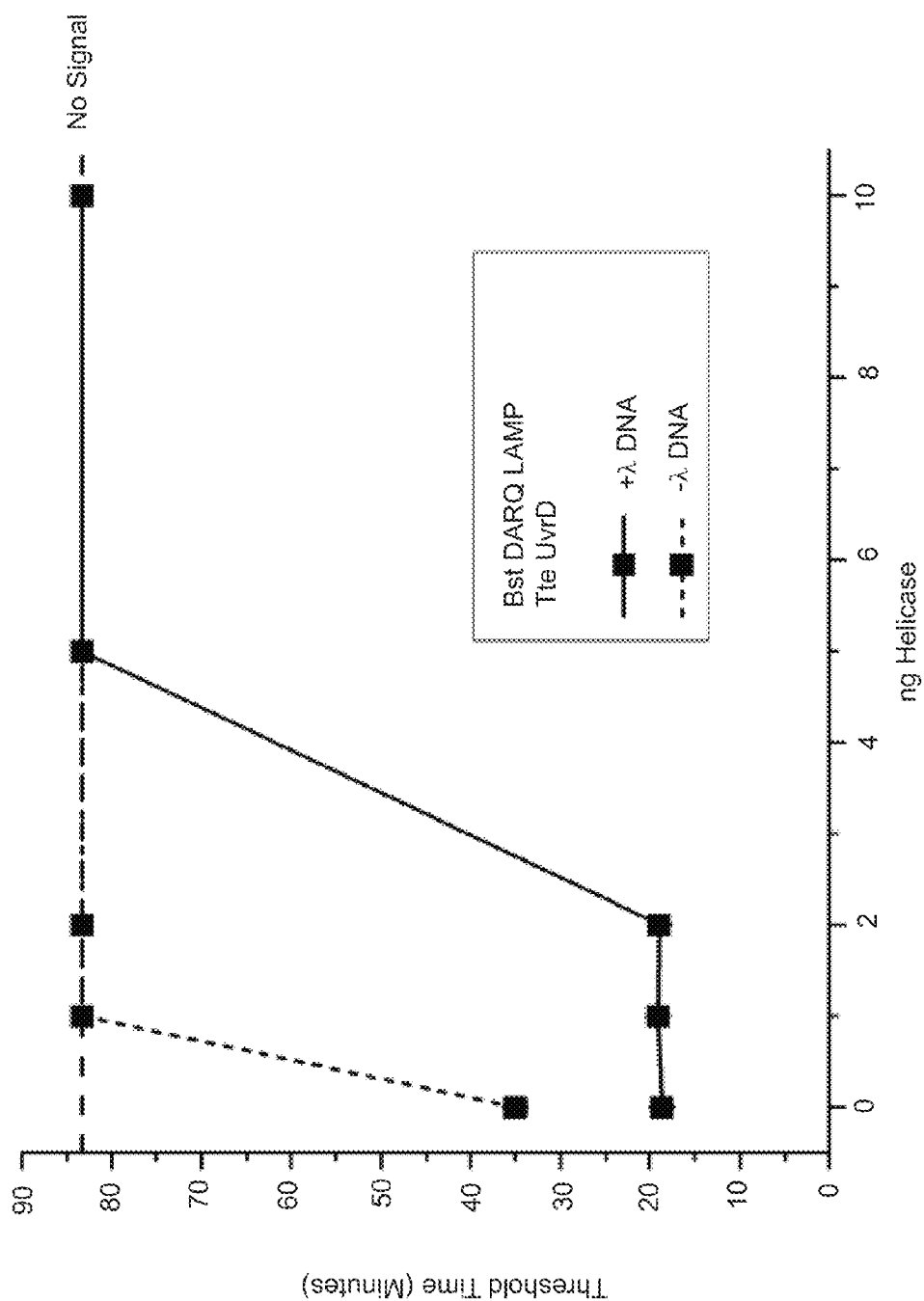

FIG. 5 shows the effect of a helicase on suppressing non-template amplification in LAMP reactions using DARQ probe primers (Tanner, et al., *BioTechniques*, 53:81-89 (2012)). Threshold time in minutes is plotted on the y-axis against nanograms of Tte helicase on the x-axis. Reactions containing template (lambda) DNA are represented by solid lines and reactions without template dashed lines. As shown, without helicase negative reactions resulted in threshold time of approximately 35 minutes while positive reactions gave threshold time of approximately 20 minutes. With addition to a 25 µl reaction mixture of 1-2 ng Tte helicase, a positive threshold time of 20 minutes is maintained while negative reactions are completely inhibited (graphed as maximum reaction time, 83.3 minutes). Addition of >2 ng of helicase to a 25 µl reaction mixture inhibited the amplification of target DNA.

Figure 6:
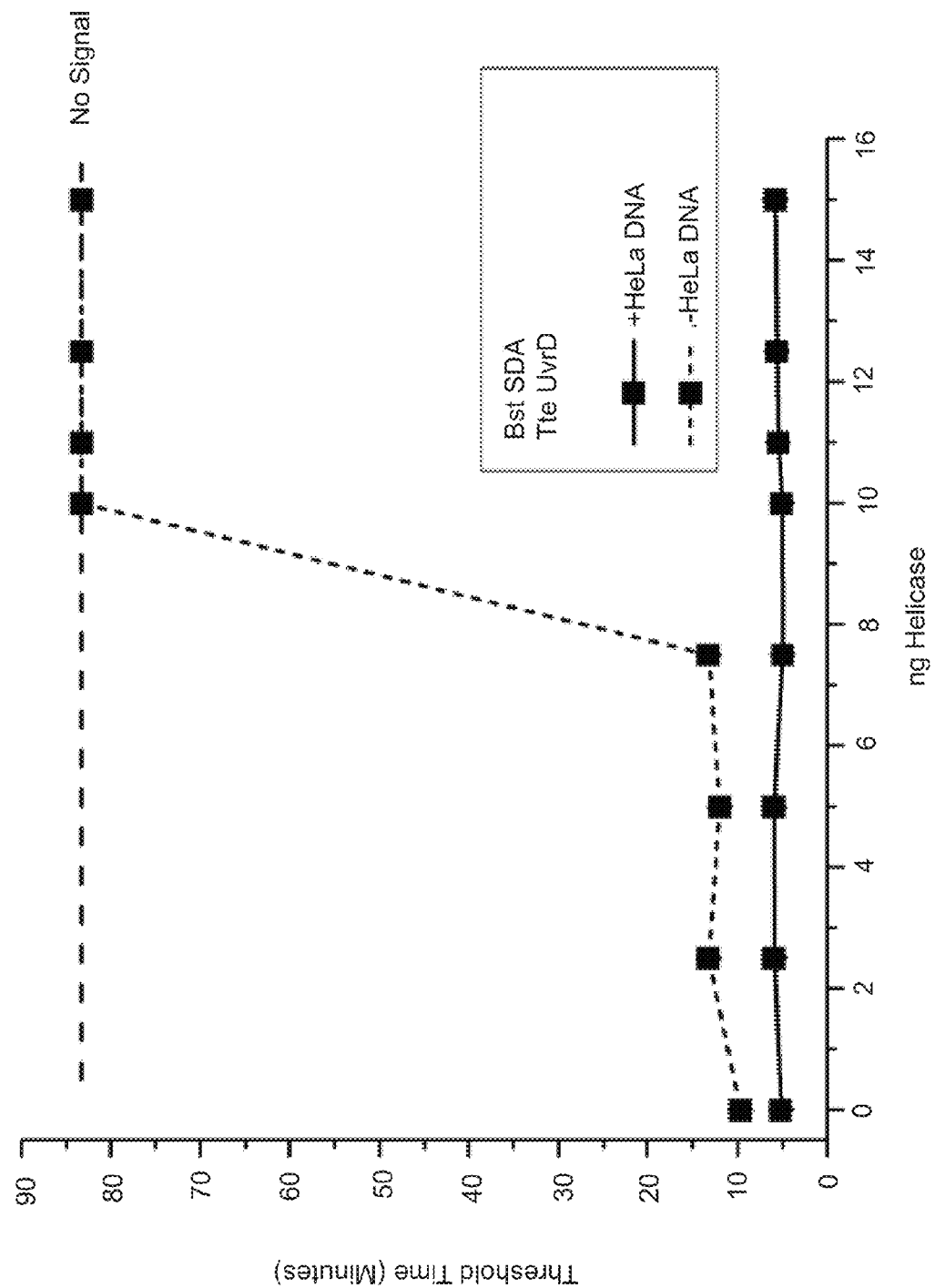

FIG. 6 shows the effect of helicase on non-template amplification in strand displacement amplification (SDA) reactions. Reactions were performed with Bst DNA polymerase and BsoBl restriction enzyme. Threshold time in minutes is plotted on the y-axis against nanograms of Tte helicase on the x-axis. Reactions containing template (HeLa) DNA resulted in rapid threshold times (solid lines), as did negative reactions without template DNA (dashed lines). With addition of >8 ng Tte helicase to a 25 µl reaction mixture, rapid amplification with template DNA was maintained, but negative reactions were completely inhibited (graphed as total reaction time, 42 minutes, for comparison). This indicates that the effect of helicase on non-template amplification is applicable to other amplification techniques, including multi-enzyme systems.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., *Dictionary of Microbiology and Molecular Biology*, 2d ed. John Wiley and Sons, New York (1994), and Hale & Markham, *The Harper Collins Dictionary of Biology*, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "an enzyme" refers to one or more enzymes, i.e., a single enzyme and multiple enzyme. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "nucleic acid sample" refers to a sample that contains nucleic acid. A nucleic acid sample may contain DNA (e.g., genomic DNA or an enriched fraction thereof) or RNA (e.g., total RNA or an enriched fraction thereof such as polyA$^+$ RNA). A nucleic acid sample may be obtained from any source. In some cases a nucleic acid sample may be obtained from a mammal (e.g., from a clinical sample such as a biopsy or the like), cultured cells, or from the environment. The nucleic acid in the sample may be from any species, e.g., from an animal (e.g., a mammal such as a human), plant, or a microbe.

As used herein, the term "template" or "target" refers to a nucleic acid in a sample that is targeted for amplification. The nucleic acid is copied in the amplification process.

As used herein, the term "non-template molecules" refers to nucleic acid in a sample that is not targeted for amplification. Such molecules may be amplified by, for example, one or more primers annealing to a non-complementary site in the sample (i.e., by "mis-priming").

As used herein, the term "nucleotides" refers to a composition containing deoxyribonucleotides corresponding to G, A, T and C, as well as analogs thereof.

As used herein, the term "four or more primers" refers to four or more oligonucleotides that have a 3' hydroxyl and are capable of being extended by a polymerase. In many cases, a primer may be 5 to 100 nt in length. Depending on the method used, a primer may be sequence-specific. In other cases, a primer may be designed to hybridize to sequences in multiple targets. Four or more primers include 5 or more primers, 6 or more primers, 7 or more primers, 8 or more primers, etc.

As used herein, the term "single-stranded DNA binding protein" (SSBP) refers to a protein that binds to single-stranded DNA and prevents two complementary strands of single stranded DNA from annealing to one another. The genomes of most organisms, including bacteria (e.g., *E. coli*), viruses (e.g., herpes viruses) and mammals, encode at least one SSBP.

As used herein, "not helicase dependent" refers to an amplification reaction which proceeds (i.e., is capable amplifying a target sequence) in the absence of helicase but nonetheless reveals a higher background from non-template DNA than would otherwise be observed in the presence of helicase.

As used herein, the term "capable of amplifying" refers to a reaction mixture that contains all necessary reagents (e.g., buffer, cofactors, etc.) for amplifying a template under the amplification conditions used.

As used herein, the term "isothermal amplification" is intended to refer to a DNA amplification reaction that does not require a denaturation step after the reaction has started. More specifically, isothermal amplification methods do not require a thermostable polymerase and do not involve thermocycling, i.e., cycling between a denaturation temperature of above 90° C. and an annealing/extension temperature. Isothermal amplification reactions employ a strand-displacing polymerase and are incubated at a temperature that is below 90° C. for a period of time (e.g., 5 minutes to 12 hours or more). Some isothermal amplification reactions are performed at a temperature of 30° C. to 60° C. while others are performed at a temperature in the range of 50° to 80° C. While examples of isothermal amplification provided herein specify LAMP and SDA and isothermal amplification method known in the art that does not absolutely require helicase is intended to be included within the meaning of this term.

As used herein the terms "loop-mediated isothermal amplification" and "LAMP" refer to the isothermal amplification method the principle of which is described in Notomi, et al, Nucl. Acids. Res., 28: e63 (2000)), which is incorporated by reference herein. In LAMP, a strand-displacing DNA polymerase initiates synthesis, and two of the primers form loop structures to facilitate subsequent rounds of amplification. The final products of LAMP are stem-loop DNAs that contain several inverted repeats of the target.

As used herein, the term "PCR conditions" refers to reaction conditions that require thermocycling, i.e., cycling between a denaturation temperature of above 90° C. and an annealing/extension temperature that is usually in the range of 50° to 80° C. PCRs require a thermostable polymerase.

As used herein, the term "whole genome amplification" refers to a non-specific isothermal amplification reaction that essentially amplifies all nucleic acid in a sample.

As used herein, the term "target fragments" refers to one or more specific sequences in a sample (e.g., one or more genes) that are targeted for amplification using sequence-specific primers.

Unless indicated to the contrary, reference to a particular enzyme (e.g., a reference to Tte helicase, Taq polymerase, 9° N polymerase PolD polymerase, phi29 polymerase, or Bst polymerase etc.) is intended to encompass the wild type enzyme as well as variants of the wild type enzyme that are functional and have an amino acid sequence that is at least 95% identical to the wild type enzyme, and fusions thereof. Included in this definition are chimeric proteins such as a polymerase containing a polymerase domain and a DNA binding domain from different sources (such as for Bst polymerase, Bst-Sso7d, PolD-Sso7d, KOD-Sso-7; and Tgo-Sso7d). Alternatively, the enzymes may be fused to an affinity domain or other peptide sequence which does not impair and may enhance the activity of the enzyme.

In some cases, variants are known in the art. In other cases, variants can be readily designed from sequence alignments and other information that is known in the art.

Other definitions of terms may appear throughout the specification.

DETAILED DESCRIPTION OF EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Addition of a helicase to non-helicase-dependent amplification reactions was found to eliminate detectable amplification of non-template polynucleotide including DNA or RNA with no inherent limit on types of target sequences. This effect is not amplification method specific. The effect is consistently observed for isothermal amplification reactions. In each of the examples provided below, which are not intended to be limiting, but are illustrative of the general nature of the effect, the helicase inhibited non-target DNA amplification. The inhibition of false positive signals using a helicase is also expected to occur in PCR reactions. The helicase can be added to an amplification reaction mixture containing a DNA polymerase and optionally a reverse transcriptase together with primers and other standard reagents for amplification including quantitative amplification of nucleic acids.

Non-template amplification is commonly observed in real-time quantitative amplification methods and has the effect of reducing detection sensitivity thresholds, producing false-positive amplification, and obscuring signal from target nucleic acids. Non-template amplification occurs in amplification reactions using non-template primers and adapters including hairpin primers, DARQ probes (Tanner (2012)), and linear primers.

Helicase suppression of non-template amplification may be achieved for any amplification protocol including SDA, nicking enzyme amplification reaction (NEAR), LAMP, multiple displacement amplification (MDA) and rolling circle amplification (RCA), recombinase polymerase amplification (RPA) or non-isothermal methods, e.g. PCR. Amplification procedures that require helicase to amplify the target nucleic acid (see for example, U.S. Pat. No. 7,282,328; An, et al., J Biol Chem, 208(32):28952-28958 (2005)) are not included herein.

Helicase suppression of non-template amplification can be achieved in amplification reactions that utilize a range of polymerases such as Family A and Family B polymerases in the amplification reaction. For example, the mixture was effective in amplifications using Family A Bst polymerase and derivatives thereof (New England Biolabs, Ipswich, Mass.); Family B PolD (such as mutant 9° N (New England Biolabs, Ipswich, Mass.)).

Helicase suppression of non-template amplification can be achieved in the presence of different sized nucleic acid template sequences and for various nucleic acid template sequences contained in longer nucleic acids from plasmid, viral DNA, prokaryotic and eukaryotic DNA.

Concentrations of helicase for addition to an amplification protocol may be greater than 0.04 ng/µL, 0.08 ng/µL, 0.12 ng/µL, 0.16 ng/µL, 0.20 ng/µL, 0.24 ng/µL, 0.28 ng/µL, 0.32 ng/µL, 0.36 ng/µL, 0.40 ng/µL, 0.44 ng/µL, 0.48 ng/µL, 0.52 ng/µL, 0.56 ng/µL 0.60 ng/µL, 0.64 ng/µL in an amplification reaction mixture (see Example 1).

Different helicases from the PcrA/UvrD/Rep helicase subfamily were tested and all of these were found to cause a similar effect of suppression of non-template DNA. Examples include bacterial helicases such as Tte UvrD helicase, Tth UvrD helicase, Aq793 PUR helicase, UvrD helicase from *Thermus aquaticus* or archaeal helicases such as, PUR helicase from *Thermococcus kodakarensis* (SEQ ID NO:22), PUR helicase from *Thermococcus litoralis*, and PUR helicase from *Pyrococcus furiosis*. Although single helicases were tested, more than one helicase may be used in a single reaction for the desired suppression, hence use of "a" helicase may include "one or more" helicases. Other examples of PcrA/UvrD/Rep helicases are described in U.S. Pat. No. 7,282,328 which may be used in the present methods for preventing false positive signals and are herein incorporated by reference.

The ability to prevent detectable non-template amplification results in an increase in sensitivity of detection of amplified target DNA. This increase can be as much as 2 fold, 3 fold, 4 fold, 5 fold, 10 fold, 20 fold, 30 fold, 40 fold, 50 fold, 60 fold, 70 fold, 80 fold, 90 fold or 100 fold or greater.

Helicase suppression of non-template amplification was effective when the target DNA was the product of reverse transcription of RNA even when the amplification reaction included a reverse transcriptase. Helicase suppression of non-template amplification was effective in quantitative amplification conditions as demonstrated herein using probe-based detection methods such as DARQ.

Helicase suppression of non-template amplification may be achieved using standard polymerase buffers containing, for example 10 mM-250 mM KCl at pH 7.5-pH 10 and at temperatures in the range of 15° C. to 72° C. for isothermal amplification or temperatures of 50° C. to 95° C. for PCRs.

Helicase suppression of non-template amplification provides an effective enhancement of diagnostic sensitivity in a clinical setting as well as a research tool.

Consistent with the above, a reaction mixture for amplifying a template nucleic acid from a sample is provided. In certain embodiments, the reaction mixture comprises a) a nucleic acid sample comprising a template; b) nucleotides; c) four or more primers; d) a polymerase; and e) a helicase. The reaction mixture is characterized in that it does not contain a SSBP regardless of whether the helicase is thermostable or not. The reaction mixture is capable of amplifying the template when it is placed under isothermal or PCR conditions in the presence or absence of a helicase.

In certain embodiments, the helicase may be a thermostable helicase, i.e., a helicase encoded by the genome of a thermophilic organism. In some cases, the helicase may be a PcrA/UvrD/Rep helicase. In particular embodiments, the helicase may be selected from the group consisting of a Tte helicase, Tth helicase and Aq793 helicase.

The polymerase in the reaction mixture may be chosen depending on the how the reaction mixture is to be used (e.g., whether it is to be subjected to isothermal or PCR reaction conditions). The polymerase may be thermostable or not thermostable, strand-displacing or not strand-displacing and, in some cases, the polymerase may be proofreading or not proofreading, and, in some cases, may have an inactivated 3' to 5' exonuclease activity. In some embodiments, the polymerase is not *E. coli* DNA polymerase I or the Klenow fragment of that polymerase. In some embodiments, the polymerase is not T4 DNA polymerase. In some cases, the polymerase may be Bst polymerase or phi29 polymerase.

Depending on the desired application, the primers in the reaction mixture may be sequence specific or non-sequence specific. A reaction mixture may contain a single primer, at least two primers, at least three primers, at least 4 primers or at least 5 primers (e.g., in the case of a multiplex reaction).

The template in the reaction mixture may be genomic DNA, cDNA or RNA. In some embodiments, the polymerase may be an RNA polymerase and, certain cases, the reaction mixture may contain an RNA polymerase and a DNA polymerase.

A method for reducing amplification of non-template molecules from a nucleic acid sample is provided. In certain embodiments, this method comprises making the above-described reaction mixture (i.e., by combining reagents in a vessel) and incubating the reaction mixture under amplification conditions to amplifying the template. In this method, the presence of the helicase reduces amplification of non-template molecules.

In some embodiments, the amplification conditions used may be isothermal amplification conditions. In these embodiments, the polymerase may be a strand-displacing polymerase and the reaction mixture may be incubated at a temperature in the range of 50° C. to 80° C. for a period of time, e.g., from 10 minutes to overnight. Depending on how the method is implemented, the method may result in whole genome amplification or amplification of one or more target sequences, e.g., from cDNA or a genome.

In other embodiments, the amplification conditions may comprise thermocycling. In these embodiments, the polymerase may be a thermostable polymerase, and the reaction may be incubated at a temperate that varies between a first temperature in the range of 90° C. to 96° C. (during which the template denatures), and a second temperate in the range of 40° C. to 80° C. (during which the polymerase extends primers that have annealed to the template). Conditions for performing PCR are well known.

In other embodiments, the polymerase may be a reverse transcriptase, and the method may result in reverse transcription of an RNA template. In particular cases, the reaction mix may contain all the necessary components for performing RT-PCR (i.e., at least two primers, a reverse transcriptase and a DNA polymerase). In these embodiments, the method may result in amplification of an RNA template by RT-PCR.

In certain embodiments, the method may further involve quantifying the amount of amplified product. This may be done by any convenient product, e.g., end-point PCR or qPCR or the like.

All references cited herein, as well as U.S. provisional application Ser. No. 61/840,287, filed on Jun. 27, 2013, are incorporated by reference.

EXAMPLES

Aspects of the present teachings can be further understood in light of the following examples, which should not be construed as limiting the scope of the present teachings in any way.

Example 1: Reduction of Background Signal from Non-Template Amplification in LAMP The LAMP assay was performed as follows: LAMP primers designed for bacteriophage lambda DNA at 1.6 µM Forward internal primer (FIP)/Back internal primer (BIP); 0.2 µM Forward external primer (F3)/Back external primer (B3); 0.4 µM Forward loop primer (LoopF)/Back loop primer (LoopB) were prepared in LAMP buffer [20 mM Tris, 50 mM KCl, 10 mM $(NH_4)_2SO_4$, 8 mM $MgSO_4$, 1.4 mM dNTPs, 0.1% Tween-20® (Sigma-Aldrich, St. Louis, Mo.), pH 8.8 25° C.] (see below for primer sequences).

DNA polymerase was added at 0.4-8 ng/µl or 0.04-0.64 Units/µl polymerase (e.g. Bst large fragment DNA polymerase, Bst 2.0, Bst-Sso7d, PolD; all from New England Biolabs, Ipswich, Mass.). Positive reactions contained 5 ng-5 fg Lambda DNA as the template (New England Biolabs, Ipswich, Mass.). The negative control contained NTC. The reaction mixture further included 0.04-0.8 ng/µL helicase (See FIG. 3 for a comparison of Tte helicase, Tth helicase, or Aq helicase, all produced at New England Biolabs, Ipswich, Mass.).

The reactions were performed at a final volume of 25 µL. The reactions were incubated at 65° C. for typically about 85 minutes. The extent of amplification of a lambda DNA amplicon with a size of 100-200 bases was measured for this period of time to permit 250 cycles of DNA concentration measurements in a BioRad CFX96™ real-time fluorescence instrument (Bio-Rad, Hercules, Calif.) for detecting SYTO-9® (Life Technologies, Carlsbad, Calif.) double strand DNA intercalating dye (Nagamine, et al., *Molecular and Cellular Probes*, 16:223-229 (2002)) added to the buffer at a concentration of 2 µM at the same time as the enzymes in the reaction. Detection of amplification product was substantially complete by 25-30 minutes but an extended time was used to ensure that any non-template amplification products were detected.

The following primers were used:

```
Lambda Primers
FIP:
                                          (SEQ ID NO: 1)
CAGCCAGCCGCAGCACGTTCGCTCATAGGAGATATGGTAGAGCCGC BIP:
                                          (SEQ ID NO: 2)
GAGAGAATTTGTACCACCTCCCACCGGGCACATAGCAGTCCTAGGGACA
GT F3:
                                          (SEQ ID NO: 3)
GGCTTGGCTCTGCTAACACGTT B3:
                                          (SEQ ID NO: 4)
GGACGTTTGTAATGTCCGCTCC LoopF:
                                          (SEQ ID NO: 5)
CTGCATACGACGTGTCT LoopB:
                                          (SEQ ID NO: 6)
ACCATCTATGACTGTACGCC
```

Figure 1:
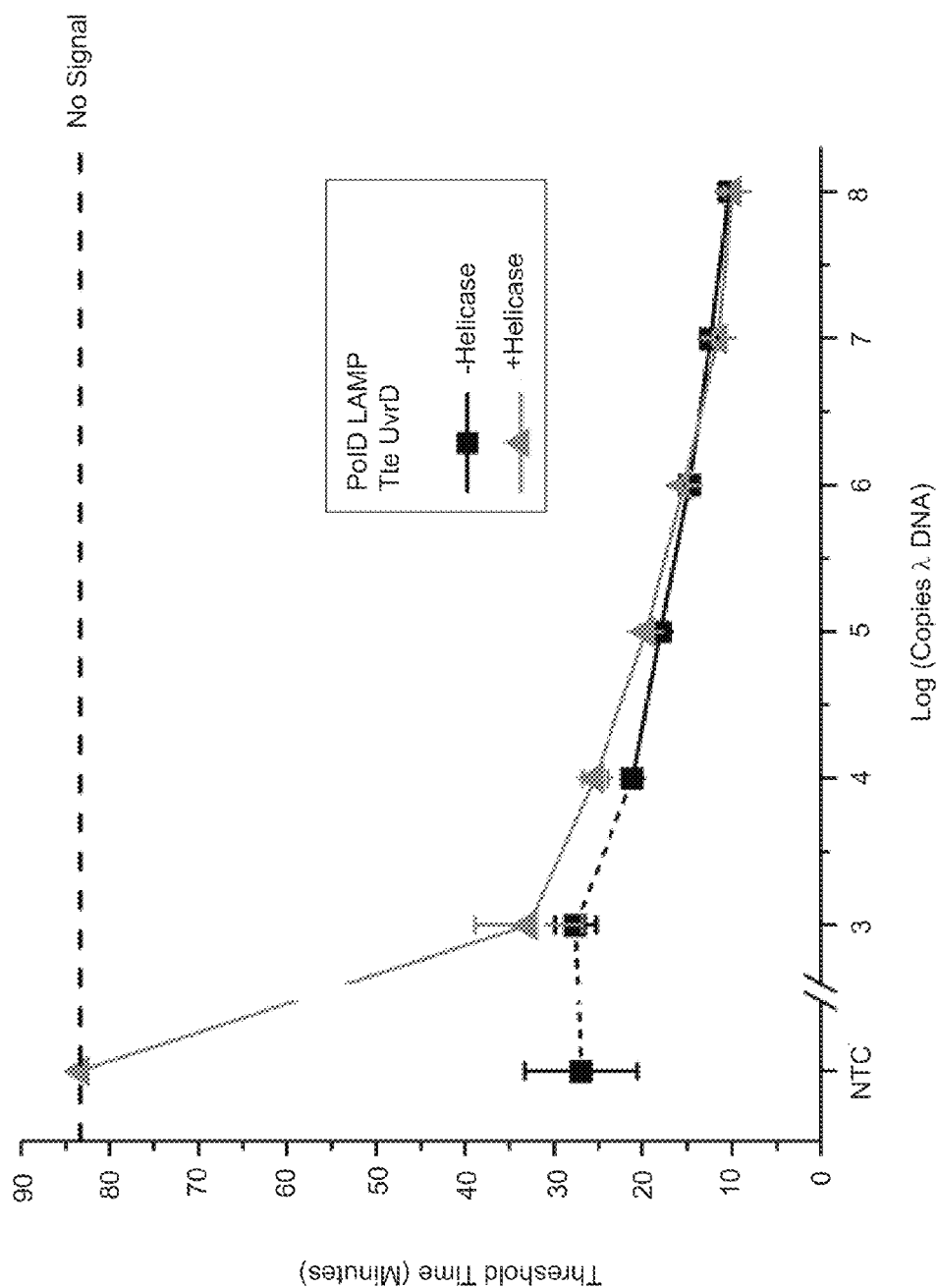
FIG. 1 shows improvement in diagnostic sensitivity gained from the addition of a helicase in loop-mediated isothermal amplification (LAMP) with PolD DNA polymerase. The y-axis is threshold time (minutes) for detection of amplification product and the x-axis is the log of copies of template DNA. An increased threshold time is proportional to decreased template copy number. Reactions without helicase are represented as black squares and with helicase as grey triangles. The break in the x-axis indicates a gap between 1,000 copy reaction and reaction with no template DNA (NTC). As shown, reaction time without helicase at low template concentration is indistinguishable from reaction time with no template, resulting in a loss of detection sensitivity. In contrast, addition of 2 ng Tte helicase to a 25 μl reaction mixture enables the 1,000 copy reaction to provide a threshold time while the false positive signal from the NTC reaction is inhibited and yields no threshold (plotted as maximum reaction time, 83.3 minutes, indicated by "No Signal" line). This improvement in distinction represents a 10-fold improvement in sensitivity, as lower limit of detection without helicase is 10,000 copies but with helicase 1,000 copies.
Figure 2:
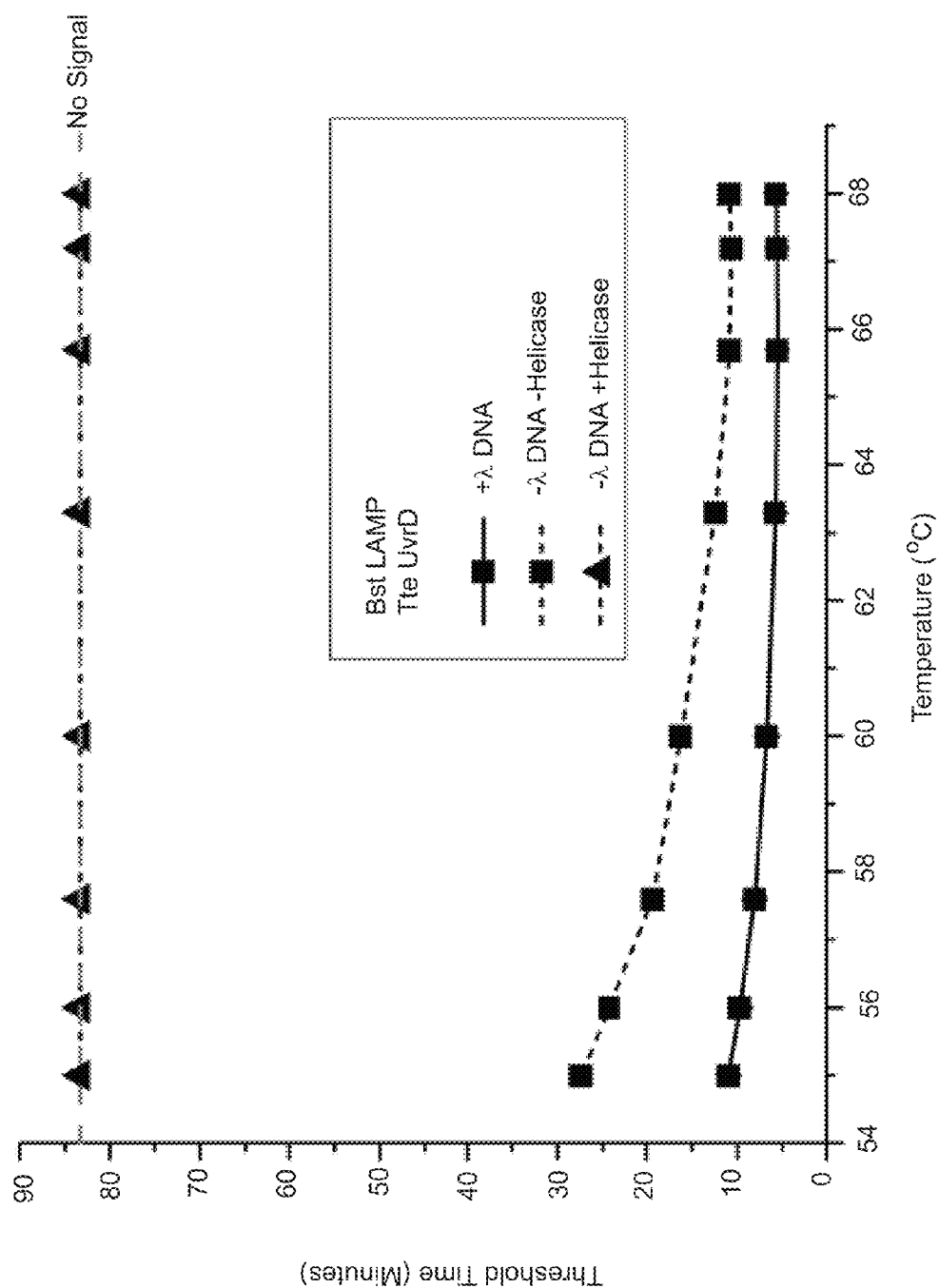
FIG. 2 shows that the addition of helicase to a 25 μl reaction mixture eliminates non-template amplification at all relevant LAMP temperatures. Threshold time in minutes is plotted on the y-axis against temperature in degrees Celsius on the x-axis. Squares represent reactions without helicase, with template DNA (solid line) and without (dashed). Triangles represent negative reactions containing 8 ng of Tte helicase, which gave no amplification signal but are plotted as maximum reaction time (83.3 minutes, grey line) for comparison. Positive reactions gave rapid threshold times at all temperatures (55° C. to 68° C.), but without helicase, negative reactions resulted in thresholds only slightly slower. Addition of helicase to reactions without template resulted in no amplification and thus no threshold time, providing absolute discrimination between positive and negative reactions across the temperature range.
Figure 3A:
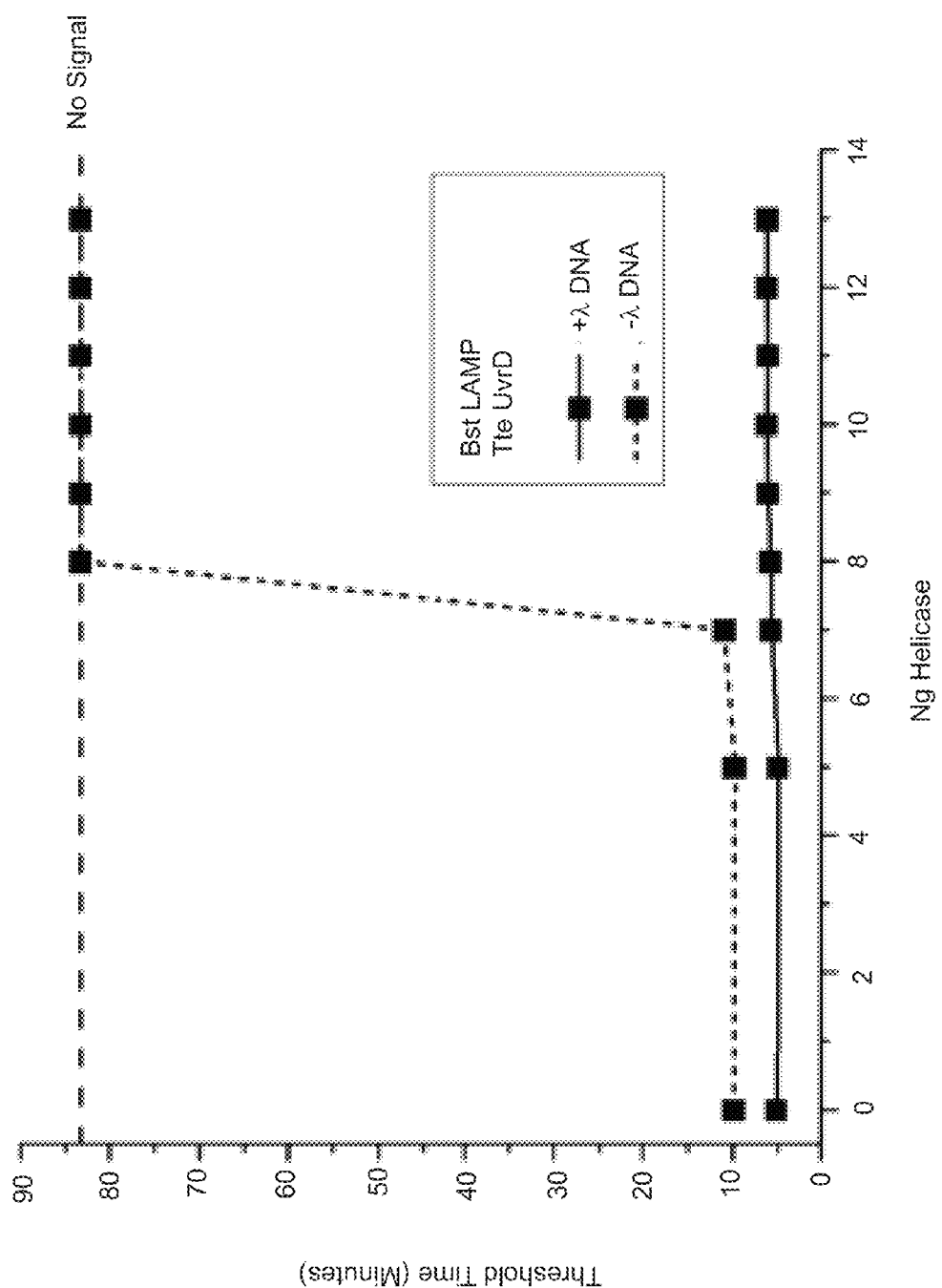
FIG. 3A-C show that each of the three UrD helicases tested reduced non-template amplification in LAMP reactions. Threshold time in minutes is plotted on the y-axis against increasing amounts of Tte helicase (FIG. 3A), Tth helicase (FIG. 3B) or Aq793 helicase (FIG. 3C). The results show a similar titration pattern, with a threshold concentration of helicase producing a sudden break in threshold times to a level of no background amplification from non-template DNA using different helicases.
Figure 3B:
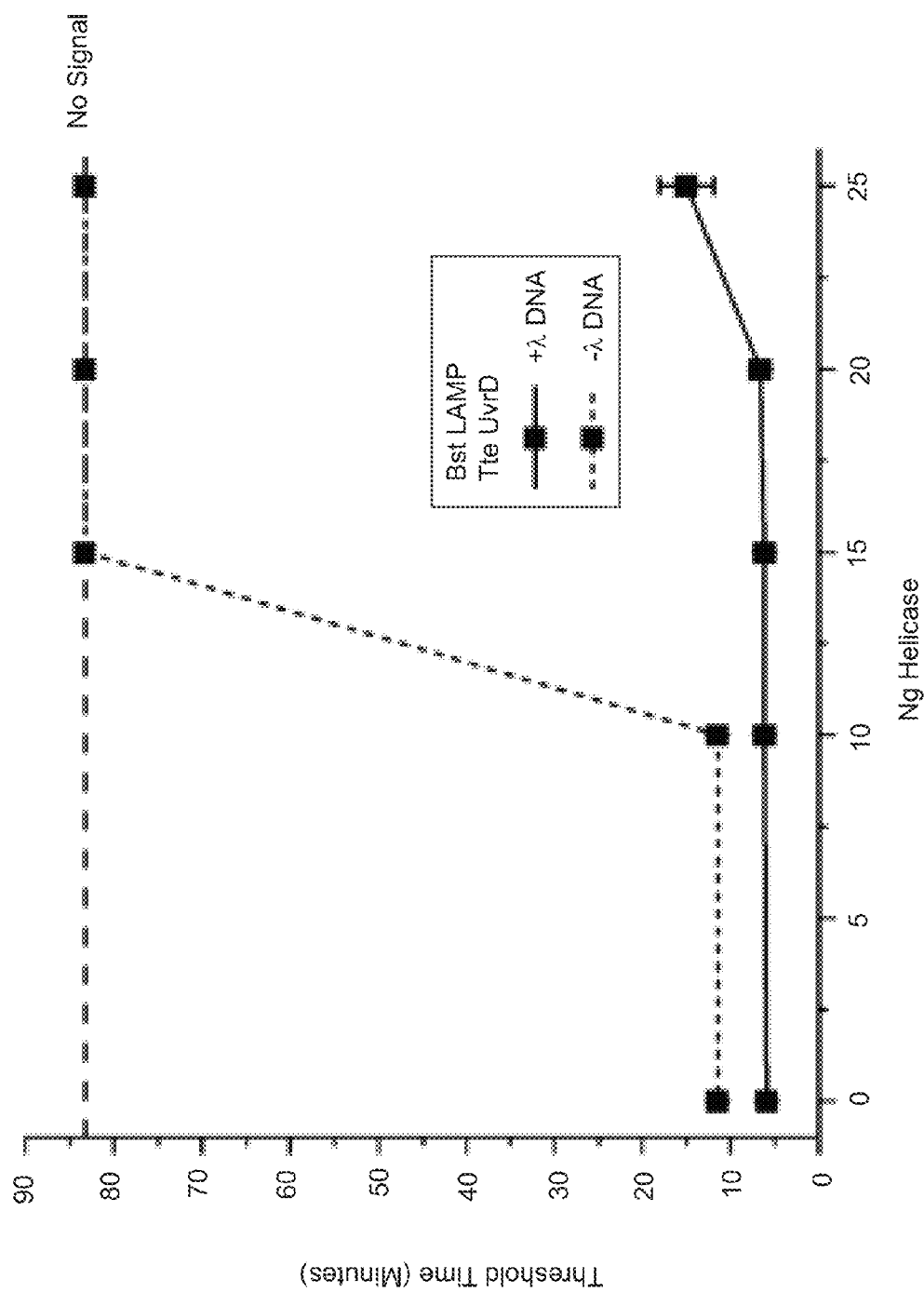
Figure 3C:
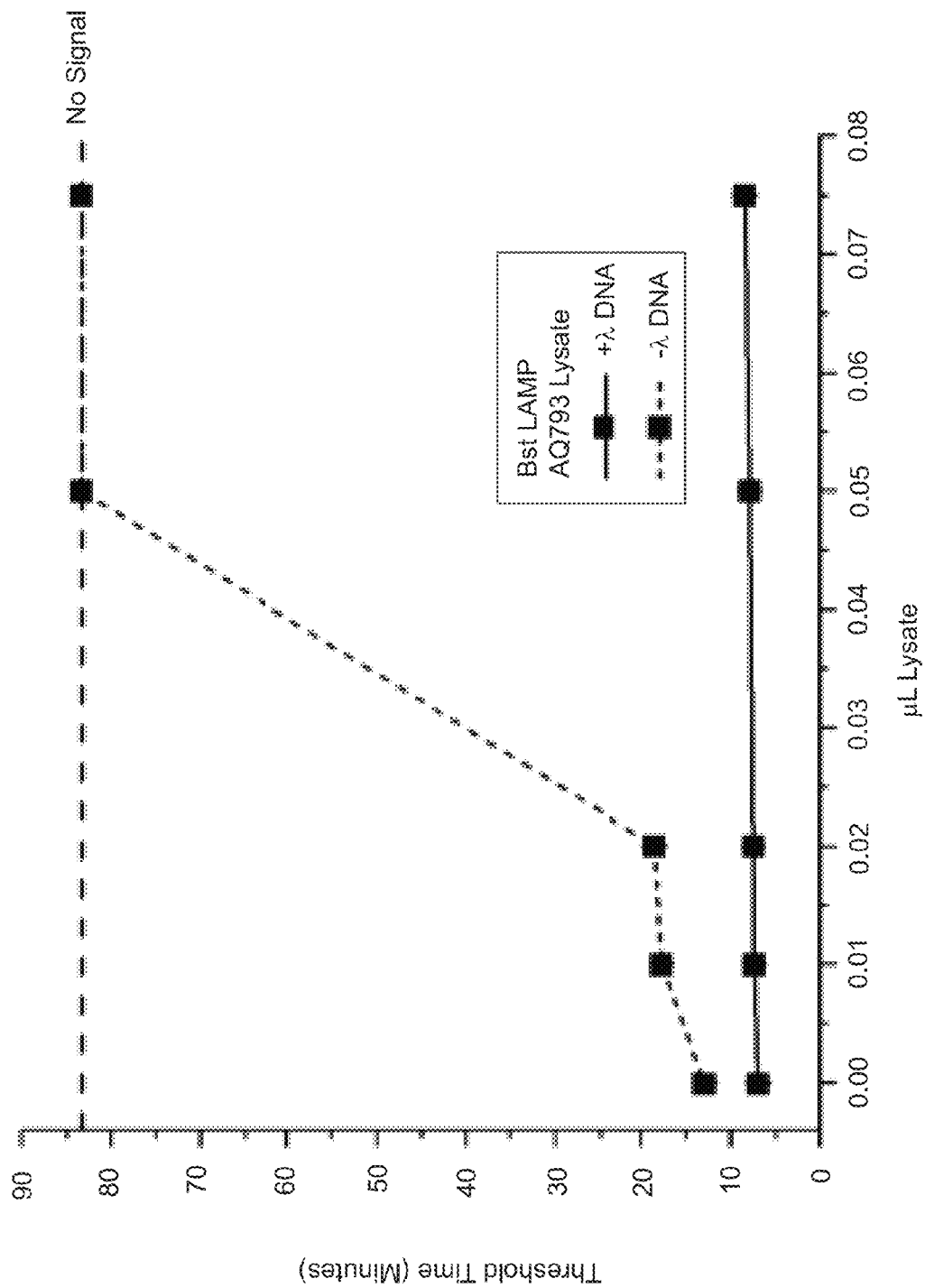

The reduction in background signal from non-template amplification was quantitatively assessed (see FIGS. 1-3A-C). In the absence of helicase, a positive signal for an amplification product of a template was detected at about 5 to 10 minutes at temperature 65° C. and for a non-template signal at 20 to 30 minutes (FIGS. 1 and 2). Varying amounts of helicase was included in the amplification mixture (0.32-0.60 ng/µL helicase with Bst; (0.52-0.80 ng/µL Bst-Sso7d; or 0.1-28 ng/µL PolD), to produce a positive signal for template amplification at 5 to 10 minutes with complete suppression of detectable signal of non-template amplification products even after 83.3 minutes for non-template reactions (FIG. 3). The maximum time of 83 minutes (on the Y-axis of FIGS. 1-3) was provided to illustrate the complete suppression of detectable non-template amplification. For convenience of graphing, a negative result for amplification was represented by a signal at this time point.

For measuring sensitivity of the amplification protocol for template DNA with reduced background from amplification of non-template DNA, reactions were performed with varying amounts of template (lambda DNA) which were 5 ng ($10^8$ copies) to 5 pg (100 copies) (see FIG. 1). Without addition of a helicase, the lower limit of detection of the template above background negative control was $10^4$ copies. In the presence of a helicase, $10^3$ copies of the template DNA provided robust detection of amplification above background negative control (with helicase but no DNA). The negative control produced no signal. FIG. 3 shows comparable performance of three different helicases used under these conditions. This represents a significant diagnostic improvement for LAMP reactions, with higher level of sensitivity and discrimination between positive and negative reactions.

Example 2: Reduction of Background Signal from Non-Template Amplification in RT-LAMP The reaction conditions were the same as in Example 1 except that a reverse transcriptase was added to the enzyme mixture containing DNA polymerase and helicase (0.2 U/µL reverse transcriptase (AMV RT, New England Biolabs, Ipswich, Mass.)) and different LAMP primers were used and are described below. Template RNA used was 10 ng Jurkat total RNA (BioChain, San Francisco, Calif.). Negative control reactions contained no template RNA. In this example, Tte helicase was used at 0.04-0.6 ng/μL.

Amplification was measured by fluorescence from 2 μM SYTO-9 in the buffer as described in Example 1. Primers were designed for BRCA1 gene using LAMP primer design software (PrimerExplorer, Eiken, Japan):

```
BRCA Primers
FIP:
                                           (SEQ ID NO: 7)
ATCCCCAGTCTGTGAAATTGGGCAAAATGCTGGGATTATAGATGT BIP:
                                           (SEQ ID NO: 8)
GCAGCAGAAAGATTATTAACTTGGGCAGTTGGTAAGTAAATGGAAGA F3:
                                           (SEQ ID NO: 9)
TCCTTGAACTTTGGTCTCC B3:
                                          (SEQ ID NO: 10)
CAGTTCATAAAGGAATTGATAGC LoopF
                                          (SEQ ID NO: 11)
AGAACCAGAGGCCAGGCGAG LoopB:
                                          (SEQ ID NO: 12)
AGGCAGATAGGCTTAGACTCAA
```

The reduction in background signal from non-template amplification was quantitatively assessed and shown in FIG. 4. The total reaction time for LAMP was 83.3 minutes. In the absence of helicase, a positive signal for an amplification product of a template could be detected at about 10 minutes at temperature of 65° C. and for a non-template signal at approximately 30 minutes. When 0.32 ng/μL Tte helicase was included in the amplification mixture a positive signal for template amplification was still seen at 10 minutes but no signal was seen even after 83.3 minutes for non-template reactions. The maximum time of 83 minutes (on the Y-axis of FIG. 4) was provided to illustrate the complete suppression of detectable non-template amplification. For convenience of graphing, a negative result for amplification was represented by a signal at this time point.

This demonstrates that the elimination of non-template amplification extends to reactions using RNA templates, exemplified by RT-LAMP. Sequence-specific amplification of RNA is a significant area of molecular diagnostic and biological research, and improvements in reaction specificity are advantageous in these applications.

Example 3: Reduction in Background Signal from Non-Template Amplification in Probe-Based DARQ LAMP Detection The reaction conditions were the same as in Example 1 except for the use of two additional primers, primer concentrations as described below and Bst 2.0 DNA polymerase concentration of 0.64 U/μL.

Eight primers were used instead of 6 primers. The additional two primers were a 5'-fluorophore labeled FIP and a 3'-dark quencher labeled FIP complementary sequence (Fd) to form a DARQ detection duplex.

The concentration of the primers used was 0.8 μM Forward internal primer (FIP), 0.8 μM 5'-fluorophore FIP, 0.8 μM 3'-dark quencher Fd, 1.6 μM Back internal primer (BIP), 0.2 μM Forward external primer (F3)/Back external primer (B3), 0.4 μM Forward loop primer (LoopF)/Back loop primer (LoopB). 5 ng lambda template DNA were included in the sample 25 μL reaction mixture or NTC was added to the control. 0.04-0.1 ng/μL Tte helicase was added to determine suppression of the non template DNA and the reaction incubated at 65° C. for about 83 minutes as described in Example 1.

Amplification of lambda amplicon was measured by increase in fluorescence from dequenching as DARQ primer probe duplex were separated due to strand displacement activity (see for example, Tanner, et al, (2012); US publication No. 2014/0031248). In this example, FIP primer was labeled with HEX dye and F1-complementary Fd probe labeled with IowaBlack®-FQ dark quencher (Integrated DNA Technologies, Coralville, Iowa).

```
Lambda DARQ Primers
FIP:
                                           (SEQ ID NO: 1)
CAGCCAGCCGCAGCACGTTCGCTCATAGGAGATATGGTAGAGCCGC Fluorophore-FIP:
                                          (SEQ ID NO: 13)
5'-HEX-CAGCCAGCCGCAGCACGTTCGCTCATAGGAGATATGGTAGAGC
CGC Quencher-Fd:
                                          (SEQ ID NO: 14)
CGAACGTGCTGCGGCTGGCTG-IABkFQ-3

BIP:
                                           (SEQ ID NO: 2)
GAGAGAATTTGTACCACCTCCCACCGGGCACATAGCAGTCCTAGGGACA
GT

F3:
                                           (SEQ ID NO: 3)
GGCTTGGCTCTGCTAACACGTT

B3:
                                           (SEQ ID NO: 4)
GGACGTTTGTAATGTCCGCTCC

LoopF:
                                           (SEQ ID NO: 5)
CTGCATACGACGTGTCT LoopB:
                                           (SEQ ID NO: 6)
ACCATCTATGACTGTACGCC
```

Increase in fluorescence due to amplification was measured using channel 2 of Bio-Rad CFX96 Real-Time instrument. Threshold was defined automatically by increase in fluorescence above subtracted background, and is plotted as threshold time in FIG. 5.

Without addition of helicase positive reactions gave amplification threshold time of approximately 20 minutes and negative reaction threshold time of approximately 35 minutes. With addition of 0.04-0.08 ng/μL Tte helicase, positive amplification threshold time for target nucleic acid was maintained at about 20 minutes and negative reactions for non-target nucleic acid gave no amplification signal or threshold. This was plotted in FIG. 5 as total reaction time, 83.3 minutes, for purposes of comparison.

Example 4: Reduction of Background Signal from Non-Template Amplification in SDA SDA amplification reactions were performed in SDA buffer [35 mM $K_iPO_4$, 8 mM MgOAc], 0.4 mM dATP, 0.4 mM dGTP, 0.4 mM dTTP, 0.8 mM 2'-deoxycytidine-5'-O-thiotriphosphate (dCTP-αS, TriLink BioTechnologies, San Diego, Calif.)]. Enzymes added were 0.16 U/μL DNA polymerase (Bst large fragment) and 1.7 U/μL BsoBI (New England Biolabs, Ipswich, Mass.). SDA Primers for human BRCA1 were added at 0.5 μM Forward SDA primer (S1), 0.5 μM reverse SDA primer (S2), 0.5 μM forward bump primer (B1), 0.5 μM reverse bump primer (B2). The template DNA in the reaction was 100 ng HeLa genomic DNA (New England Biolabs, Ipswich, Mass.) or none for negative control reactions. Tte helicase was added at 0.04-0.4 ng/μL and reactions were incubated at 65° C. to 71° C.

Amplification of the BRCA amplicon was measured by real-time fluorescence from 2 μM SYTO-9 recorded by a Bio-Rad CFX96 real-time florescence instrument using the following primers. S1 and S2 contain the BsoBI recognition site in non-target region at 5' ends, which was used as a nicking site by hemi-cleavage due to incorporation of phosphorothioate linkage on bottom strand.

```
BRCA SDA Primers
S1:
                                            (SEQ ID NO: 15)
ACCGCATCGAATGCATGTCTCGGGCAAAATGCTGGGATTATAGATGT S2:
                                            (SEQ ID NO: 16)
GGATTCCGCTCCAGACTTCTCGGGCAGTTGGTAAGTAAATGGAAGA B1:
                                            (SEQ ID NO: 17)
TCCTTGAACTTTGGTCTCC B2:
                                            (SEQ ID NO: 18)
CAGTTCATAAAGGAATTGATAGC
```

The reduction in background signal from non-template amplification was quantitatively assessed and the results are shown in FIG. 6. The total reaction time for SDA was 45 minutes. In the absence of helicase, a positive signal for an amplification product of a template could be detected at about 2-4 minutes at temperature 65° C. to 71° C. (Bst DNA polymerase), and for a non-template signal at 5 minutes to 10 minutes. When an effective amount of helicase was included in the amplification mixture (0.1-0.8 ng/μLng helicase with Bst DNA polymerase), a positive signal for template amplification was still seen at 2-4 minutes but no signal was seen even after 45 minutes for non-template reactions. This is recorded as the maximum time to illustrate the effect. However, for convenience of graphing purpose, whenever the amplification signal did not appear after 45 minutes, it is marked as if amplification signal appeared at this time point even though there was no signal observed.

In summary the efficacy of helicase in suppressing non-template amplification was demonstrated using various methods of amplification. SDA produced discrete amplicon products using a multi-enzyme system for amplification.

```
>SEQ ID NO: 19; Helicase 1
MIGVKKMKEILANLNEQQKEAVTTTEGPLLILAGAGSGKTRVLTHRIAYL

IKEKKVSPSNILAITFTNKAAEEMKTRVENLLGYVGDLWVSTFHSACVRI

LRRDIDKLGYDRNFVIFDTTDQKALVQECLKELDLSEKQYPIKMVLNAIS

SAKDKMVYPDDYIDFFGDTYRNRKIKEIYKLYQHKLKKINALDFDDIIIK

TIELFKENPEILEFYQRKFRYIMVDEYQDTNTPQYYFVNLLAQRHRNLCV

VGDDDQSIYGWRGADVRNILNFEKDYPEAKVIKLEQNYRSTKIILEAANH

VIDNNVYRKKKSLWTQNKEGEKIVLCELENEREEAEFVIQEIIKLKEREN

RSFKDFAILYRTNAQSRPFEEALMKVKVPYKVVGALRFYDRKEIKDILAY

LRLIVNPYDDISFKRIVNVPRRGIGPATIEALEKVAREKDTSLFFAIEDL

KNARNKGSLLQFKQFILDLIDKKDAMSVSDLIKYILEQTGYIEELKREES

EEAEGRIENLNEFLNAAYEFEESSEDKSLEAFLAGITLVSDIDMAGDIGE

SVVLMTLHSAKGLEFPVVFMVGMEEGLFPSYSSFEDDHELEEERRLCYVG

ITRSKERLYLTYARQRNLYGRSQYNSYSRFISEIPERLIVRYNIPTSKKT

GFVSVHTFSDVYERSFSLGDKVEHKIWGIGTVVKVEGEEITVAFPNVGIK

KLDLRFAPIKAIS

>SEQ ID NO: 20; Helicase 2
MSDALLAPLNEAQRQAVLHFEGPALVVAGAGSGKTRTVVHRVAYLVARRG

VFPSEILAVTFTNKAAEEMRERLRGLVPGAGEVWVSTFHAAALRILRVYG

ERVGLRPGFVVYDEDDQTALLKEVLKELALSARPGPIKALLDRAKNRGVG

LKALLGELPEYYAGLSRGRLGDVLVRYQEALKAQGALDFGDILLYALRLL

EEDEEVLRLVRKRARFIHVDEYQDTSPVQYRFTRLLAGEEANLMAVGDPD

QGIYSFRAADIKNILDFTRDYPEARVYRLEENYRSTEAILRFANAVIVKN

ALRLEKALRPVKRGGEPVRLYRAEDAREEARFVAEEIARLGPPWDRYAVL

YRTNAQSRLLEQALAGRGIPARVVGGVGFFERAEVKDLLAYARLALNPLD

AVSLKRVLNTPPRGIGPATWRVQLLAQEKGLPPWEALKEAARTFPRAEPL

RHFVALVEELQDLVFGPAEAFFRHLLEATDYPTYLREAYPEDAEDRLENV

EELLRAAKEAEDLQDFLDRVALTAKAEEPAEAEGKVALMTLHNAKGLEFP

VVFLVGVEEGLLPHRNSLSTLEGLEEERRLFYVGITRAQERLYLSHAEER

EVYGRREPARPSRFLEEVEEGLYEVYDPYRRPPSPPPHRPRPGAFRGGER

VVHPRFGPGTVVAAQGDEVTVHFEGVGLKRLSLKYAELKP

>SEQ ID NO: 21; Helicase 3
MKLNTQQEEAVRHFGSPLLVVAGAGSGKTKTLTHKVEYLIKEKGLKPYEI

LCITFTNKAAKEIKERIKNTFGLELEWSGTFHSVALKILKKDGEKIGIPK

DFSIADEKDTTLIVKEILKKYGLKKEPEEVKEKISKVKENFEEPEAWLGV

LLEEYQRVLRENKLLDFSDLMRELYNLLLVDEVREKYRNTFKYIMVDEYQ

DTNNIQYEILKLLANKNICAIGDPNQCIYEWRDARPDNILRFIEDFNPKI

IKLELNYRSREPILRVANAVLEASTLEWKDLIPKLRGVRGEGQKPYVRRF

QDEEEEALWISRKIKELAGEYELKDIAVLVRVGYITDVFERTFFKAGIPY

KVVGTIKFYERIEIKNLIALLRLIYNPSDEVAFKRLTEFFVKGFGDKSFE

VVKKNFKGNWFKALKESLKKLPKNAAISAYEFLKAVVPLYKNPEKYHEGL

EAFVEKIDYYELLKEKFKKDYEERIENVKEFLSSLKDFYAKAYTLEDLLA

EITLTSEEEEENAVKILTIHSAKGLEFPVVFLPRLEEGILPHHRSQESE

RELEEERRLFYVAITRAKDLLFMSYTKKENRKPSRFLSDIPKHLLDLSAF

KKKKKVAYEENLRPNRLIKKGDKVIHRVFGKGVVLRIEEERAKVRFENGE

EKVIHTSFLEPLKTPSGVP

>SEQ ID NO: 22; Helicase 4
MNEKEVLLSKFIAHLKELVEMERRAEIEAMRLEMRRLSGREREKVGRAVL
```

-continued

GLNGKVIGEELGYFLVRYGRDREIKTEISVGDLVVISKRDPLKSDLVGTV

VEKGKRFLTVAIETVPEWALKGVRIDLYANDITFKRWMENLDNLRESGRK

ALELYLGLREPEESEPVEFQPFDKSLNASQRGAIAKALGSGDFFLVHGPF

GTGKTRTLVELIRQEVARGHKVLATAESNVAVDNIVERLADSGLKVVRIG

HPSRVSKALHETTLAYLITQHDLYAELRELRVIGENLKEKRDTFTKPAPK

YRRGLSDREILRLAEKGIGTRGVPARLIREMAEWIRINQQVQKTFDDARK

-continued

LEERIAREIIQEADVVLTTNASAGLEVVDYGEYDVAVIDEATQATIPSVL

IPINRAKRFVLAGDHKQLPPTILSEKAKELSKTLFEGLIERYPEKSEMLT

VQYRMNERLMEFPSREFYDGKIKAHESVKNITLADLGVSEPEFGNFWDEA

LKPENVLVFIDTSKREDRFERQRRGSDSRENPLEAKLVTETVEKLLEMGV

KPDWIGVITPYDDQRDLISSMVGEDIEVKTVDGYQGREKEIIVLSFVRSN

RRGELGFLTDLRRLNVSLTRAKRKLIAVGDSSTLSNHPTYRRFIEFVRER

GTFIEIDGKKH

The invention claimed is:

1. A reaction mixture comprising:
   a) a nucleic acid sample comprising a template;
   b) nucleotides;
   c) four or more primers;
   d) a polymerase; and
   e) a non-thermostable helicase;
   wherein the reaction mixture does not contain a single-stranded DNA binding protein (SSBP) and wherein the reaction mixture is capable of amplifying the template when placed under isothermal or polymerase chain reaction conditions.

2. The reaction mixture of claim 1, wherein the helicase is a PcrA/UvrD/Rep helicase.

3. The reaction mixture of claim 1, wherein the polymerase is a strand-displacing polymerase.

4. The reaction mixture of claim 3, wherein the polymerase is selected from the group consisting of a Bst polymerase, a polD polymerase, a 9° N polymerase and phi29 polymerase.

5. The reaction mixture of claim 1, wherein the polymerase is a thermostable polymerase.

6. The reaction mixture of claim 1, wherein the template is RNA and the polymerase is a reverse transcriptase.

7. The reaction mixture of claim 1, wherein the template is genomic DNA.

8. A method for reducing amplification of non-template molecules from a nucleic acid sample, comprising:
   a) incubating a reaction mixture of claim 1 under amplification conditions, and
   b) amplifying the template; wherein the amplification reaction is not helicase dependent but wherein the helicase reduces amplification of non-template molecules.

9. The method of claim 8, wherein the amplification conditions are isothermal amplification conditions.

10. The method of claim 8, wherein (b) results in whole genome amplification.

11. The method of claim 8, wherein (b) results in amplification of one or more target fragments of a genome or cDNA.

12. The method of claim 8, wherein the amplification conditions comprise thermocycling.

13. The method of claim 8, wherein (b) results in reverse transcription of an RNA template.

14. The method of claim 13, wherein (b) results in amplification of an RNA template by RT-PCR.

15. The method of claim 8, wherein the method further comprises quantifying the amount of amplified template after (b).

16. The method of claim 8, wherein the helicase is a PcrA/UvrD/Rep helicase.

17. The method of claim 8, wherein the polymerase is selected from the group consisting of a Bst polymerase, a polD polymerase, 9° N polymerase and phi29 polymerase.

18. The method of claim 8, wherein the reaction mixture is a loop-mediated isothermal amplification (LAMP) reaction mixture.

19. A loop-mediated isothermal amplification (LAMP) reaction mixture comprising:
   a) a nucleic acid sample comprising a template;
   b) nucleotides;

c) four or more primers;
d) a polymerase; and
e) a helicase;
wherein the reaction mixture optionally contains a single-stranded DNA binding protein (SSBP) and wherein the reaction mixture is capable of amplifying the template by LAMP.

20. The LAMP reaction mixture of claim 19, wherein the mixture comprises six or more primers.

* * * * *

SEQUENCE LISTING

<160> NUMBER OF SEQ ID NOS: 22

<210> SEQ ID NO 1
<211> LENGTH: 46
<212> TYPE: DNA
<213> ORGANISM: enterobacteria phage

<400> SEQUENCE: 1
cagccagccg cagcacgttc gctcatagga gatatggtag agccgc      46

<210> SEQ ID NO 2
<211> LENGTH: 51
<212> TYPE: DNA
<213> ORGANISM: enterobacteria phage

<400> SEQUENCE: 2
gagagaattt gtaccacctc ccaccgggca catagcagtc ctagggacag t      51

<210> SEQ ID NO 3
<211> LENGTH: 22
<212> TYPE: DNA
<213> ORGANISM: enterobacteria phage

<400> SEQUENCE: 3
ggcttggctc tgctaacacg tt      22

<210> SEQ ID NO 4
<211> LENGTH: 22
<212> TYPE: DNA
<213> ORGANISM: enterobacteria phage

<400> SEQUENCE: 4
ggacgtttgt aatgtccgct cc      22

<210> SEQ ID NO 5
<211> LENGTH: 17
<212> TYPE: DNA
<213> ORGANISM: enterobacteria phage

<400> SEQUENCE: 5
ctgcatacga cgtgtct      17

<210> SEQ ID NO 6
<211> LENGTH: 20
<212> TYPE: DNA
<213> ORGANISM: enterobacteria phage

<400> SEQUENCE: 6
accatctatg actgtacgcc      20

<210> SEQ ID NO 7
<211> LENGTH: 45
<212> TYPE: DNA
<213> ORGANISM: Homo sapiens

<400> SEQUENCE: 7
atccccagtc tgtgaaattg ggcaaaatgc tgggattata gatgt        45

<210> SEQ ID NO 8
<211> LENGTH: 47
<212> TYPE: DNA
<213> ORGANISM: Homo sapiens

<400> SEQUENCE: 8
gcagcagaaa gattattaac ttgggcagtt ggtaagtaaa tggaaga        47

<210> SEQ ID NO 9
<211> LENGTH: 19
<212> TYPE: DNA
<213> ORGANISM: Homo sapiens

<400> SEQUENCE: 9
tccttgaact ttggtctcc        19

<210> SEQ ID NO 10
<211> LENGTH: 23
<212> TYPE: DNA
<213> ORGANISM: Homo sapiens

<400> SEQUENCE: 10
cagttcataa aggaattgat agc        23

<210> SEQ ID NO 11
<211> LENGTH: 20
<212> TYPE: DNA
<213> ORGANISM: Homo sapiens

<400> SEQUENCE: 11
agaaccagag gccaggcgag        20

<210> SEQ ID NO 12
<211> LENGTH: 22
<212> TYPE: DNA
<213> ORGANISM: Homo sapiens

<400> SEQUENCE: 12
aggcagatag gcttagactc aa        22

<210> SEQ ID NO 13
<211> LENGTH: 46
<212> TYPE: DNA
<213> ORGANISM: enterobacteria phage

<400> SEQUENCE: 13
cagccagccg cagcacgttc gctcatagga gatatggtag agccgc        46

<210> SEQ ID NO 14
<211> LENGTH: 21
<212> TYPE: DNA
<213> ORGANISM: enterobacteria phage

<400> SEQUENCE: 14
cgaacgtgct gcggctggct g        21

<210> SEQ ID NO 15
<211> LENGTH: 46
<212> TYPE: DNA
<213> ORGANISM: Homo sapiens

<400> SEQUENCE: 15
ccgcatcgaa tgcatgtctc gggcaaaatg ctgggattat agatgt         46

<210> SEQ ID NO 16
<211> LENGTH: 46
<212> TYPE: DNA
<213> ORGANISM: Homo sapiens

<400> SEQUENCE: 16
ggattccgct ccagacttct cgggcagttg gtaagtaaat ggaaga         46

<210> SEQ ID NO 17
<211> LENGTH: 19
<212> TYPE: DNA
<213> ORGANISM: Homo sapiens

<400> SEQUENCE: 17
tccttgaact ttggtctcc         19

<210> SEQ ID NO 18
<211> LENGTH: 23
<212> TYPE: DNA
<213> ORGANISM: Homo sapiens

<400> SEQUENCE: 18
cagttcataa aggaattgat agc         23

<210> SEQ ID NO 19
<211> LENGTH: 713
<212> TYPE: PRT
<213> ORGANISM: Thermoanaerobacter tengcongensis

<400> SEQUENCE: 19

Met Ile Gly Val Lys Lys Met Lys Glu Ile Leu Ala Asn Leu Asn Glu
1               5                   10                  15

Gln Gln Lys Glu Ala Val Thr Thr Thr Glu Gly Pro Leu Leu Ile Leu
            20                  25                  30

Ala Gly Ala Gly Ser Gly Lys Thr Arg Val Leu Thr His Arg Ile Ala
        35                  40                  45

Tyr Leu Ile Lys Glu Lys Lys Val Ser Pro Ser Asn Ile Leu Ala Ile
    50                  55                  60

Thr Phe Thr Asn Lys Ala Ala Glu Glu Met Lys Thr Arg Val Glu Asn
65                  70                  75                  80

Leu Leu Gly Tyr Val Gly Asp Leu Trp Val Ser Thr Phe His Ser Ala
                85                  90                  95

Cys Val Arg Ile Leu Arg Arg Asp Ile Asp Lys Leu Gly Tyr Asp Arg
            100                 105                 110

Asn Phe Val Ile Phe Asp Thr Thr Asp Gln Lys Ala Leu Val Gln Glu
        115                 120                 125

Cys Leu Lys Glu Leu Asp Leu Ser Glu Lys Gln Tyr Pro Ile Lys Met
    130                 135                 140

Val Leu Asn Ala Ile Ser Ser Ala Lys Asp Lys Met Val Tyr Pro Asp
145                 150                 155                 160

-continued

```
Asp Tyr Ile Asp Phe Phe Gly Asp Thr Tyr Arg Asn Arg Lys Ile Lys
            165                 170                 175
Glu Ile Tyr Lys Leu Tyr Gln His Lys Leu Lys Ile Asn Ala Leu
        180                 185                 190
Asp Phe Asp Asp Ile Ile Ile Lys Thr Ile Glu Leu Phe Lys Glu Asn
    195                 200                 205
Pro Glu Ile Leu Glu Phe Tyr Gln Arg Lys Phe Arg Tyr Ile Met Val
210                 215                 220
Asp Glu Tyr Gln Asp Thr Asn Thr Pro Gln Tyr Phe Val Asn Leu
225                 230                 235                 240
Leu Ala Gln Arg His Arg Asn Leu Cys Val Val Gly Asp Asp Gln
                245                 250                 255
Ser Ile Tyr Gly Trp Arg Gly Ala Asp Val Arg Asn Ile Leu Asn Phe
            260                 265                 270
Glu Lys Asp Tyr Pro Glu Ala Lys Val Ile Lys Leu Glu Gln Asn Tyr
        275                 280                 285
Arg Ser Thr Lys Ile Ile Leu Glu Ala Ala Asn His Val Ile Asp Asn
    290                 295                 300
Asn Val Tyr Arg Lys Lys Lys Ser Leu Trp Thr Gln Asn Lys Glu Gly
305                 310                 315                 320
Glu Lys Ile Val Leu Cys Glu Leu Glu Asn Glu Arg Glu Ala Glu
                325                 330                 335
Phe Val Ile Gln Glu Ile Ile Lys Leu Lys Glu Arg Glu Asn Arg Ser
            340                 345                 350
Phe Lys Asp Phe Ala Ile Leu Tyr Arg Thr Asn Ala Gln Ser Arg Pro
        355                 360                 365
Phe Glu Glu Ala Leu Met Lys Val Lys Val Pro Tyr Lys Val Val Gly
    370                 375                 380
Ala Leu Arg Phe Tyr Asp Arg Lys Glu Ile Lys Asp Ile Leu Ala Tyr
385                 390                 395                 400
Leu Arg Leu Ile Val Asn Pro Tyr Asp Asp Ile Ser Phe Lys Arg Ile
                405                 410                 415
Val Asn Val Pro Arg Arg Gly Ile Gly Pro Ala Thr Ile Glu Ala Leu
            420                 425                 430
Glu Lys Val Ala Arg Glu Lys Asp Thr Ser Leu Phe Phe Ala Ile Glu
        435                 440                 445
Asp Leu Lys Asn Ala Arg Asn Lys Gly Ser Leu Leu Gln Phe Lys Gln
    450                 455                 460
Phe Ile Leu Asp Leu Ile Asp Lys Lys Asp Ala Met Ser Val Ser Asp
465                 470                 475                 480
Leu Ile Lys Tyr Ile Leu Glu Gln Thr Gly Tyr Ile Glu Glu Leu Lys
                485                 490                 495
Arg Glu Glu Ser Glu Glu Ala Glu Gly Arg Ile Glu Asn Leu Asn Glu
            500                 505                 510
Phe Leu Asn Ala Ala Tyr Glu Phe Glu Glu Ser Ser Glu Asp Lys Ser
        515                 520                 525
Leu Glu Ala Phe Leu Ala Gly Ile Thr Leu Val Ser Asp Ile Asp Met
    530                 535                 540
Ala Gly Asp Ile Gly Glu Ser Val Val Leu Met Thr Leu His Ser Ala
545                 550                 555                 560
Lys Gly Leu Glu Phe Pro Val Val Phe Met Val Gly Met Glu Glu Gly
                565                 570                 575
Leu Phe Pro Ser Tyr Ser Ser Phe Glu Asp Asp His Glu Leu Glu Glu
```

```
              580                 585                 590
Glu Arg Arg Leu Cys Tyr Val Gly Ile Thr Arg Ser Lys Glu Arg Leu
            595                 600                 605

Tyr Leu Thr Tyr Ala Arg Gln Arg Asn Leu Tyr Gly Arg Ser Gln Tyr
            610                 615                 620

Asn Ser Tyr Ser Arg Phe Ile Ser Glu Ile Pro Glu Arg Leu Ile Val
625                 630                 635                 640

Arg Tyr Asn Ile Pro Thr Ser Lys Lys Thr Gly Phe Val Ser Val His
            645                 650                 655

Thr Phe Ser Asp Val Tyr Glu Arg Ser Phe Ser Leu Gly Asp Lys Val
            660                 665                 670

Glu His Lys Ile Trp Gly Ile Gly Thr Val Val Lys Val Glu Gly Glu
            675                 680                 685

Glu Ile Thr Val Ala Phe Pro Asn Val Gly Ile Lys Lys Leu Asp Leu
            690                 695                 700

Arg Phe Ala Pro Ile Lys Ala Ile Ser
705                 710

<210> SEQ ID NO 20
<211> LENGTH: 690
<212> TYPE: PRT
<213> ORGANISM: Thermus thermophilus

<400> SEQUENCE: 20

Met Ser Asp Ala Leu Leu Ala Pro Leu Asn Glu Ala Gln Arg Gln Ala
1               5                   10                  15

Val Leu His Phe Glu Gly Pro Ala Leu Val Val Ala Gly Ala Gly Ser
            20                  25                  30

Gly Lys Thr Arg Thr Val Val His Arg Val Ala Tyr Leu Val Ala Arg
        35                  40                  45

Arg Gly Val Phe Pro Ser Glu Ile Leu Ala Val Thr Phe Thr Asn Lys
    50                  55                  60

Ala Ala Glu Glu Met Arg Glu Arg Leu Arg Gly Leu Val Pro Gly Ala
65                  70                  75                  80

Gly Glu Val Trp Val Ser Thr Phe His Ala Ala Leu Arg Ile Leu
            85                  90                  95

Arg Val Tyr Gly Glu Arg Val Gly Leu Arg Pro Gly Phe Val Val Tyr
            100                 105                 110

Asp Glu Asp Asp Gln Thr Ala Leu Leu Lys Glu Val Leu Lys Glu Leu
            115                 120                 125

Ala Leu Ser Ala Arg Pro Gly Pro Ile Lys Ala Leu Leu Asp Arg Ala
            130                 135                 140

Lys Asn Arg Gly Val Gly Leu Lys Ala Leu Leu Gly Glu Leu Pro Glu
145                 150                 155                 160

Tyr Tyr Ala Gly Leu Ser Arg Gly Arg Leu Gly Asp Val Leu Val Arg
            165                 170                 175

Tyr Gln Glu Ala Leu Lys Ala Gln Gly Ala Leu Asp Phe Gly Asp Ile
            180                 185                 190

Leu Leu Tyr Ala Leu Arg Leu Leu Glu Glu Asp Glu Glu Val Leu Arg
            195                 200                 205

Leu Val Arg Lys Arg Ala Arg Phe Ile His Val Asp Glu Tyr Gln Asp
            210                 215                 220

Thr Ser Pro Val Gln Tyr Arg Phe Thr Arg Leu Leu Ala Gly Glu Glu
225                 230                 235                 240
```

-continued

```
Ala Asn Leu Met Ala Val Gly Asp Pro Asp Gln Gly Ile Tyr Ser Phe
                245                 250                 255
Arg Ala Ala Asp Ile Lys Asn Ile Leu Asp Phe Thr Arg Asp Tyr Pro
            260                 265                 270
Glu Ala Arg Val Tyr Arg Leu Glu Glu Asn Tyr Arg Ser Thr Glu Ala
        275                 280                 285
Ile Leu Arg Phe Ala Asn Ala Val Ile Val Lys Asn Ala Leu Arg Leu
    290                 295                 300
Glu Lys Ala Leu Arg Pro Val Lys Arg Gly Gly Glu Pro Val Arg Leu
305                 310                 315                 320
Tyr Arg Ala Glu Asp Ala Arg Glu Glu Ala Arg Phe Val Ala Glu Glu
                325                 330                 335
Ile Ala Arg Leu Gly Pro Pro Trp Asp Arg Tyr Ala Val Leu Tyr Arg
            340                 345                 350
Thr Asn Ala Gln Ser Arg Leu Leu Glu Gln Ala Leu Ala Gly Arg Gly
        355                 360                 365
Ile Pro Ala Arg Val Val Gly Val Gly Phe Phe Glu Arg Ala Glu
    370                 375                 380
Val Lys Asp Leu Leu Ala Tyr Ala Arg Leu Ala Leu Asn Pro Leu Asp
385                 390                 395                 400
Ala Val Ser Leu Lys Arg Val Leu Asn Thr Pro Pro Arg Gly Ile Gly
                405                 410                 415
Pro Ala Thr Trp Arg Val Gln Leu Leu Ala Gln Glu Lys Gly Leu Pro
            420                 425                 430
Pro Trp Glu Ala Leu Lys Glu Ala Ala Arg Thr Phe Pro Arg Ala Glu
        435                 440                 445
Pro Leu Arg His Phe Val Ala Leu Val Glu Glu Leu Gln Asp Leu Val
    450                 455                 460
Phe Gly Pro Ala Glu Ala Phe Phe Arg His Leu Leu Glu Ala Thr Asp
465                 470                 475                 480
Tyr Pro Thr Tyr Leu Arg Glu Ala Tyr Pro Glu Asp Ala Glu Asp Arg
                485                 490                 495
Leu Glu Asn Val Glu Glu Leu Leu Arg Ala Ala Lys Glu Ala Glu Asp
            500                 505                 510
Leu Gln Asp Phe Leu Asp Arg Val Ala Leu Thr Ala Lys Ala Glu Glu
        515                 520                 525
Pro Ala Glu Ala Glu Gly Lys Val Ala Leu Met Thr Leu His Asn Ala
    530                 535                 540
Lys Gly Leu Glu Phe Pro Val Val Phe Leu Val Gly Val Glu Glu Gly
545                 550                 555                 560
Leu Leu Pro His Arg Asn Ser Leu Ser Thr Leu Glu Gly Leu Glu Glu
                565                 570                 575
Glu Arg Arg Leu Phe Tyr Val Gly Ile Thr Arg Ala Gln Glu Arg Leu
            580                 585                 590
Tyr Leu Ser His Ala Glu Glu Arg Glu Val Tyr Gly Arg Arg Glu Pro
        595                 600                 605
Ala Arg Pro Ser Arg Phe Leu Glu Glu Val Glu Glu Gly Leu Tyr Glu
    610                 615                 620
Val Tyr Asp Pro Tyr Arg Arg Pro Pro Ser Pro Pro His Arg Pro
625                 630                 635                 640
Arg Pro Gly Ala Phe Arg Gly Glu Arg Val Val His Pro Arg Phe
                645                 650                 655
Gly Pro Gly Thr Val Val Ala Ala Gln Gly Asp Glu Val Thr Val His
```

```
                    660                 665                 670
Phe Glu Gly Val Gly Leu Lys Arg Leu Ser Leu Lys Tyr Ala Glu Leu
            675                 680                 685

Lys Pro
    690

<210> SEQ ID NO 21
<211> LENGTH: 669
<212> TYPE: PRT
<213> ORGANISM: Aquifex aeolicus

<400> SEQUENCE: 21

Met Lys Leu Asn Thr Gln Gln Glu Glu Ala Val Arg His Phe Gly Ser
1               5                   10                  15

Pro Leu Val Val Ala Gly Ala Gly Ser Gly Lys Thr Lys Thr Leu
            20                  25                  30

Thr His Lys Val Glu Tyr Leu Ile Lys Glu Lys Gly Leu Lys Pro Tyr
        35                  40                  45

Glu Ile Leu Cys Ile Thr Phe Thr Asn Lys Ala Ala Lys Glu Ile Lys
    50                  55                  60

Glu Arg Ile Lys Asn Thr Phe Gly Leu Glu Leu Glu Trp Ser Gly Thr
65                  70                  75                  80

Phe His Ser Val Ala Leu Lys Ile Leu Lys Lys Asp Gly Glu Lys Ile
                85                  90                  95

Gly Ile Pro Lys Asp Phe Ser Ile Ala Asp Glu Lys Asp Thr Thr Leu
            100                 105                 110

Ile Val Lys Glu Ile Leu Lys Lys Tyr Gly Leu Lys Lys Glu Pro Glu
        115                 120                 125

Glu Val Lys Glu Lys Ile Ser Lys Val Lys Glu Asn Phe Glu Glu Pro
    130                 135                 140

Glu Ala Trp Leu Gly Val Leu Glu Glu Tyr Gln Arg Val Leu Arg
145                 150                 155                 160

Glu Asn Lys Leu Leu Asp Phe Ser Asp Leu Met Arg Glu Leu Tyr Asn
                165                 170                 175

Leu Leu Leu Val Asp Glu Val Arg Glu Lys Tyr Arg Asn Thr Phe Lys
            180                 185                 190

Tyr Ile Met Val Asp Glu Tyr Gln Asp Thr Asn Asn Ile Gln Tyr Glu
        195                 200                 205

Ile Leu Lys Leu Leu Ala Asn Lys Asn Ile Cys Ala Ile Gly Asp Pro
    210                 215                 220

Asn Gln Cys Ile Tyr Glu Trp Arg Asp Ala Arg Pro Asp Asn Ile Leu
225                 230                 235                 240

Arg Phe Ile Glu Asp Phe Asn Pro Lys Ile Ile Lys Leu Glu Leu Asn
                245                 250                 255

Tyr Arg Ser Arg Glu Pro Ile Leu Arg Val Ala Asn Ala Val Leu Glu
            260                 265                 270

Ala Ser Thr Leu Glu Trp Lys Asp Leu Ile Pro Lys Leu Arg Gly Val
        275                 280                 285

Arg Gly Glu Gly Gln Lys Pro Tyr Val Arg Phe Gln Asp Glu Glu
    290                 295                 300

Glu Glu Ala Leu Trp Ile Ser Arg Lys Ile Lys Glu Leu Ala Gly Glu
305                 310                 315                 320

Tyr Glu Leu Lys Asp Ile Ala Val Leu Val Arg Val Gly Tyr Ile Thr
                325                 330                 335
```

-continued

Asp Val Phe Glu Arg Thr Phe Phe Lys Ala Gly Ile Pro Tyr Lys Val
              340                 345                 350

Val Gly Thr Ile Lys Phe Tyr Glu Arg Ile Glu Ile Lys Asn Leu Ile
          355                 360                 365

Ala Leu Leu Arg Leu Ile Tyr Asn Pro Ser Asp Glu Val Ala Phe Lys
      370                 375                 380

Arg Leu Thr Glu Phe Phe Val Lys Gly Phe Gly Asp Lys Ser Phe Glu
385                 390                 395                 400

Val Val Lys Lys Asn Phe Lys Gly Asn Trp Phe Lys Ala Leu Lys Glu
                405                 410                 415

Ser Leu Lys Lys Leu Pro Lys Asn Ala Ala Ile Ser Ala Tyr Glu Phe
              420                 425                 430

Leu Lys Ala Val Val Pro Leu Tyr Lys Asn Pro Glu Lys Tyr His Glu
          435                 440                 445

Gly Leu Glu Ala Phe Val Glu Lys Ile Asp Tyr Tyr Glu Leu Leu Lys
      450                 455                 460

Glu Lys Phe Lys Lys Asp Tyr Glu Glu Arg Ile Glu Asn Val Lys Glu
465                 470                 475                 480

Phe Leu Ser Ser Leu Lys Asp Phe Tyr Ala Lys Ala Tyr Thr Leu Glu
                485                 490                 495

Asp Leu Leu Ala Glu Ile Thr Leu Thr Ser Glu Glu Glu Glu Glu Glu
              500                 505                 510

Asn Ala Val Lys Ile Leu Thr Ile His Ser Ala Lys Gly Leu Glu Phe
          515                 520                 525

Pro Val Val Phe Leu Pro Arg Leu Glu Glu Gly Ile Leu Pro His His
      530                 535                 540

Arg Ser Gln Glu Ser Glu Arg Glu Leu Glu Glu Arg Arg Leu Phe
545                 550                 555                 560

Tyr Val Ala Ile Thr Arg Ala Lys Asp Leu Leu Phe Met Ser Tyr Thr
                565                 570                 575

Lys Lys Glu Asn Arg Lys Pro Ser Arg Phe Leu Ser Asp Ile Pro Lys
              580                 585                 590

His Leu Leu Asp Leu Ser Ala Phe Lys Lys Lys Lys Val Ala Tyr
          595                 600                 605

Glu Glu Asn Leu Arg Pro Asn Arg Leu Ile Lys Lys Gly Asp Lys Val
      610                 615                 620

Ile His Arg Val Phe Gly Lys Gly Val Val Leu Arg Ile Glu Glu Glu
625                 630                 635                 640

Arg Ala Lys Val Arg Phe Glu Asn Gly Glu Gly Lys Val Ile His Thr
                645                 650                 655

Ser Phe Leu Glu Pro Leu Lys Thr Pro Ser Gly Val Pro
              660                 665

<210> SEQ ID NO 22
<211> LENGTH: 661
<212> TYPE: PRT
<213> ORGANISM: Thermococcus kodakarensis

<400> SEQUENCE: 22

Met Asn Glu Lys Glu Val Leu Ser Lys Phe Ile Ala His Leu Lys
1               5                   10                  15

Glu Leu Val Glu Met Glu Arg Arg Ala Glu Ile Glu Ala Met Arg Leu
            20                  25                  30

Glu Met Arg Arg Leu Ser Gly Arg Glu Arg Glu Lys Val Gly Arg Ala
        35                  40                  45

```
Val Leu Gly Leu Asn Gly Lys Val Ile Gly Glu Leu Gly Tyr Phe
     50                  55                  60

Leu Val Arg Tyr Gly Arg Asp Arg Glu Ile Lys Thr Glu Ile Ser Val
65                  70                  75                  80

Gly Asp Leu Val Val Ile Ser Lys Arg Asp Pro Leu Lys Ser Asp Leu
                 85                  90                  95

Val Gly Thr Val Val Glu Lys Gly Lys Arg Phe Leu Thr Val Ala Ile
            100                 105                 110

Glu Thr Val Pro Glu Trp Ala Leu Lys Gly Val Arg Ile Asp Leu Tyr
        115                 120                 125

Ala Asn Asp Ile Thr Phe Lys Arg Trp Met Glu Asn Leu Asp Asn Leu
    130                 135                 140

Arg Glu Ser Gly Arg Lys Ala Leu Glu Leu Tyr Leu Gly Leu Arg Glu
145                 150                 155                 160

Pro Glu Glu Ser Glu Pro Val Glu Phe Gln Pro Phe Asp Lys Ser Leu
                165                 170                 175

Asn Ala Ser Gln Arg Gly Ala Ile Ala Lys Ala Leu Gly Ser Gly Asp
                180                 185                 190

Phe Phe Leu Val His Gly Pro Phe Gly Thr Gly Lys Thr Arg Thr Leu
            195                 200                 205

Val Glu Leu Ile Arg Gln Glu Val Ala Arg Gly His Lys Val Leu Ala
        210                 215                 220

Thr Ala Glu Ser Asn Val Ala Val Asp Asn Ile Val Glu Arg Leu Ala
225                 230                 235                 240

Asp Ser Gly Leu Lys Val Val Arg Ile Gly His Pro Ser Arg Val Ser
                245                 250                 255

Lys Ala Leu His Glu Thr Thr Leu Ala Tyr Leu Ile Thr Gln His Asp
            260                 265                 270

Leu Tyr Ala Glu Leu Arg Glu Leu Arg Val Ile Gly Glu Asn Leu Lys
        275                 280                 285

Glu Lys Arg Asp Thr Phe Thr Lys Pro Ala Pro Lys Tyr Arg Arg Gly
        290                 295                 300

Leu Ser Asp Arg Glu Ile Leu Arg Leu Ala Glu Lys Gly Ile Gly Thr
305                 310                 315                 320

Arg Gly Val Pro Ala Arg Leu Ile Arg Glu Met Ala Glu Trp Ile Arg
                325                 330                 335

Ile Asn Gln Gln Val Gln Lys Thr Phe Asp Asp Ala Arg Lys Leu Glu
            340                 345                 350

Glu Arg Ile Ala Arg Glu Ile Ile Gln Glu Ala Asp Val Val Leu Thr
        355                 360                 365

Thr Asn Ala Ser Ala Gly Leu Glu Val Val Asp Tyr Gly Glu Tyr Asp
    370                 375                 380

Val Ala Val Ile Asp Glu Ala Thr Gln Ala Thr Ile Pro Ser Val Leu
385                 390                 395                 400

Ile Pro Ile Asn Arg Ala Lys Arg Phe Val Leu Ala Gly Asp His Lys
                405                 410                 415

Gln Leu Pro Pro Thr Ile Leu Ser Glu Lys Ala Lys Glu Leu Ser Lys
            420                 425                 430

Thr Leu Phe Glu Gly Leu Ile Glu Arg Tyr Pro Glu Lys Ser Glu Met
        435                 440                 445

Leu Thr Val Gln Tyr Arg Met Asn Glu Arg Leu Met Glu Phe Pro Ser
        450                 455                 460
```

```
Arg Glu Phe Tyr Asp Gly Lys Ile Lys Ala His Glu Ser Val Lys Asn
465                 470                475                 480

Ile Thr Leu Ala Asp Leu Gly Val Ser Glu Pro Glu Phe Gly Asn Phe
                485                 490                 495

Trp Asp Glu Ala Leu Lys Pro Glu Asn Val Leu Val Phe Ile Asp Thr
                500                 505                 510

Ser Lys Arg Glu Asp Arg Phe Glu Arg Gln Arg Arg Gly Ser Asp Ser
        515                 520                 525

Arg Glu Asn Pro Leu Glu Ala Lys Leu Val Thr Glu Thr Val Glu Lys
        530                 535                 540

Leu Leu Glu Met Gly Val Lys Pro Asp Trp Ile Gly Val Ile Thr Pro
545                 550                 555                 560

Tyr Asp Asp Gln Arg Asp Leu Ile Ser Ser Met Val Gly Glu Asp Ile
                565                 570                 575

Glu Val Lys Thr Val Asp Gly Tyr Gln Gly Arg Glu Lys Glu Ile Ile
                580                 585                 590

Val Leu Ser Phe Val Arg Ser Asn Arg Arg Gly Glu Leu Gly Phe Leu
            595                 600                 605

Thr Asp Leu Arg Arg Leu Asn Val Ser Leu Thr Arg Ala Lys Arg Lys
        610                 615                 620

Leu Ile Ala Val Gly Asp Ser Ser Thr Leu Ser Asn His Pro Thr Tyr
625                 630                 635                 640

Arg Arg Phe Ile Glu Phe Val Arg Glu Arg Gly Thr Phe Ile Glu Ile
                645                 650                 655

Asp Gly Lys Lys His
                660
```